United States Patent
Verkman

(10) Patent No.: US 12,390,473 B2
(45) Date of Patent: Aug. 19, 2025

(54) METHODS OF TREATING TYROSINE KINASE INHIBITOR-INDUCED DIARRHEA

(71) Applicant: THE REGENTS OF THE UNIVERSITY OF CALIFORNIA, Oakland, CA (US)

(72) Inventor: Alan S. Verkman, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 332 days.

(21) Appl. No.: 17/423,444

(22) PCT Filed: Jan. 16, 2020

(86) PCT No.: PCT/US2020/013941
§ 371 (c)(1),
(2) Date: Jul. 15, 2021

(87) PCT Pub. No.: WO2020/150517
PCT Pub. Date: Jul. 23, 2020

(65) Prior Publication Data
US 2022/0088026 A1    Mar. 24, 2022

Related U.S. Application Data

(60) Provisional application No. 62/793,291, filed on Jan. 16, 2019.

(51) Int. Cl.
A61K 31/5383    (2006.01)
A61K 31/165     (2006.01)
(Continued)

(52) U.S. Cl.
CPC ........ *A61K 31/5383* (2013.01); *A61K 31/517* (2013.01); *A61P 1/12* (2018.01); *A61K 31/165* (2013.01); *A61K 31/4164* (2013.01)

(58) Field of Classification Search
CPC .................................................. A61K 31/5383
See application file for complete search history.

(56) References Cited

U.S. PATENT DOCUMENTS

| | | |
|---|---|---|
| 5,234,922 A | 8/1993 | Welsh et al. |
| 2002/0004519 A1 | 1/2002 | Lencer et al. |
| 2014/0080821 A1 | 3/2014 | Verkman et al. |

FOREIGN PATENT DOCUMENTS

| | | |
|---|---|---|
| JP | 2000-506895 A | 6/2000 |
| WO | 97/34599 A2 | 9/1997 |
| WO | 2020/150517 A2 | 7/2020 |

OTHER PUBLICATIONS

Van Sebille et al., "ErbB small molecule tyrosine kinase inhibitor (TKI) induced diarrhoea: Chloride secretion as a mechanistic hypothesis," Cancer Treatment Reviews 41(7):646-652, 2015 (Year: 2015).*

(Continued)

*Primary Examiner* — Kortney L. Klinkel
*Assistant Examiner* — Sophia Reilly
(74) *Attorney, Agent, or Firm* — Seed IP Law Group LLP

(57) ABSTRACT

The disclosure is directed to methods of treating tyrosine kinase inhibitor-induced diarrhea by administering a potassium channel inhibitor, or a CFTR chloride channel inhibitor, or a combination thereof.

10 Claims, 14 Drawing Sheets

(51) Int. Cl.
  *A61K 31/517*      (2006.01)
  *A61P 1/12*        (2006.01)
  *A61K 31/4164*     (2006.01)

(56) References Cited

OTHER PUBLICATIONS

Cil et al., "Benzopyrimido-pyrrolo-oxazine-dione CFTR inhibitor (R)-BPO-27 for antisecretory therapy of diarrheas caused by bacterial enterotoxins", FASEB journal, Feb. 2017 (Year: 2017).*
Rufo et al., "The antifungal antibiotic, clotrimazole, inhibits chloride secretion by human intestinal T84 cells via blackage of distinct basolasteral K+ conductances", J Clin Invent. 1997 (Year: 1997).*
Hirsh et al., Management of diarrhea induced by epidermal growth factor receptor tyrosine kinase inhibitors, Curr Oncol, vol. 21, No. 6, Dec. 2014 (Year: 2014).*
Charles et al., PKIBD: A Curated, Annotated and Updated Database of Protein Kinase Inhibitors in Clinical Trials, Molecules 23, Apr. 15, 2018 (Year: 2018).*
Xu et al., "Inhibition of Protein Tyrosine Phosphorylation in T Cells by a Novel Immunosuppressive agent, Leflunomide", Journal of Biological Chemistry, Feb. 1, 1995 (Year: 1995).*
Blake et al., "SU6656, a Selective Src Family Kinase Inhibitor, Used to Probe Growth Factor Signaling", Molecular and Cellular Biology, Dec. 2000, pp. 9018-9927 (Year: 2000).*
Parsons et Parsons, "SRC family kinases, key regulators of signal transduction", Oncogene, 2004 (Year: 2004).*
Guadalupe et al. "The combination astemizole-gefitinib as a potential therapy for human lung cancer" Onco Targets and Therapy Onco Targets and Therapy, 2017, 10 5795-5803. DOI: 10.2147/OTT.S144506. (Year: 2017).*
Cil et al., "Benzopyrimido-pyrrolo-oxazine-dione CFTR inhibitor (R)-BPO-27 for antisecretory therapy of diarrheas caused by bacterial enterotoxins," *The FASEB Journal* 31:751-760, Feb. 2017.
Goda et al., "The Maxi-K (BK) Channel Antagonist Penitrem A as a Novel Breast Cancer-Targeted Therapeutic," Marine Drugs 16(157): 1-21, May 11, 2018.
International Preliminary Report on Patentability, issued Jun. 16, 2021, for International Application No. PCT/US2020/013941. (18 pages).
International Search Report and Written Opinion, mailed Oct. 29, 2020, for International Application No. PCT/US2020/013941. (32 pages).
Khalid et al., "Inhibition of tumor growth and prolonged survival of rats with intracranial gliomas following administration of clotrimazole," *J. Neurosurg.* 103:79-86, Jul. 2005.
Kobayashi et al., "EGFR Exon 18 Mutations in Lung Cancer: Molecular Predictors of Augmented Sensitivity to Afatinib or Neratinib as Compared with First- or Third-Generation TKIs," *Clinical Cancer Research* 21(23):5305-5313, Dec. 1, 2015.
Ma et al., "Thiazolidinone CFTR inhibitor identified by high-throughput screening blocks cholera toxin-induced intestinal fluid secretion," The Journal of Clinical Investigation 110(11):1651-1658, Dec. 2002.

Motawi et al., "Combination of imatinib and clotrimazole enhances cell growth inhibition in T47D breast cancer cells," *Chemico-Biological Interactions* 233:147-156, 2015.
Paka et al., "Anti-steatotic and anti-fibrotic effects of the KCa3.1 channel inhibitor, Senicapoc, in non-alcoholic liver disease," *World J. Gastroenterol.* 23(23):4181-4190, Jun. 21, 2017.
Pongkorpsakol et al., "Inhibition of cAMP-Activated Intestinal Chloride Secretion by Diclofenac: Cellular Mechanism and Potential Application in Cholera," *PLOS Neglected Tropical Diseases* 8(9):e3119, pp. 1-17, Sep. 2014.
Rufo et al., "The Antifungal Antibiotic, Clotrimazole, Inhibits Chloride Secretion by Human Intestinal T84 Cells via Blockade of Distinct Basolateral $K^+$ Conductances: Demonstration of Efficacy in Intact Rabbit Colon and in an In Vivo Mouse Model of Cholera," *J. Clin. Invest.* 100(12):3111-3120, Dec. 1997.
Snyder et al., "Absolute Configuration and Biological Properties of Enantiomers of CFTR Inhibitor BPO-27," ACS Medicinal Chemistry Letters 4:456-459, Apr. 8, 2013.
Snyder et al., "Potent, Metabolically Stable Benzopyrimido-Pyrrolo-Oxazinediode (Bpo) Cftr Inhibitors for Polycystic Kidney Disease," *J. Med. Chem.* 54(15):5468-5477, Aug. 11, 2011.
Staal et al., "Inhibition of the potassium channel $K_{Ca}3.1$ by senicapoc reverses tactile allodynia in rats with peripheral nerve injury," *Eur. J. Pharmacol.* 795:1-7, 2017.
Takei et al., "Inhibitory effect of clotrimazole on angiogenesis associated with bladder epithelium proliferation in rats," *Int. J. Urol.* 10(2):78-85, 2003.
Van Sebille et al., "ErbB small molecule tyrosine kinase inhibitor (TKI) induced diarrhoea: Chloride secretion as a mechanistic hypothesis," *Cancer Treatment Reviews* 41(7):646-652, 2015.
Thiagarajah et al., "Secretory diarrhoea: mechanisms and emerging therapies," *Nat Rev Gastroenterol Hepatol.* 12(8):446-457, Aug. 2015 (HHS Public Access Author Manuscript, available in PMC Mar. 1, 20160). (24 pages).
Van Sebille et al., "Dacomitinib-induced diarrhea: Targeting chloride secretion with crofelemer", International Journal of Cancer, vol. 142, 2017, pp. 369-380.
Kharkevich et al., Farmakologiya [Pharmacology]: Textbook for higher education, 10-th edition, GEOTAR-Media, 908 p. 2010. [w/ English Translation] (32 pages).
Lexmond et al., "Electrophysiological Studies into the Safety of the Anti-diarrheal Drug Clotrimazole during Oral Rehydration Therapy," *PLoS Negl Trop Dis* 9(9):e0004098, Sep. 25, 2015. (10 pages).
Mashkovskiy, Medicaments, 14-th edition, vol. 1, Moscow, p. 11, 2002. [w/ English Translation] (3 pages).
Yakugaku Zasshi, "Physiological Role of $K^+$ Channels in the Regulation of T Cell Function," *The Pharmaceutical Society of Japan* 136(3), pp. 479-483, 2016. [w/ English Abstract] (5 pages).
Wulff et al., "Therapeutic potential of KCa3.1 blockers: an overview of recent advances, and promising trends, " Expert Rev Clin Pharmacol. 3(3):385-396, May 2010 (NIH Public Access Author Manuscript, available in PMC May 8, 2012). (20 pages).

* cited by examiner

METHODS OF TREATING TYROSINE KINASE INHIBITOR-INDUCED DIARRHEA

CROSS-REFERENCE TO RELATED APPLICATION

This application claims the benefit of priority to U.S. Provisional Application No. 62/793,291, filed Jan. 16, 2019, the entirety of which is incorporated by reference herein.

GOVERNMENT INTEREST STATEMENT

This invention was made with government support under grant nos. DK072517, DK099803, DK101373, and EB000415 awarded by the National Institutes of Health. The government has certain rights in the invention.

TECHNICAL FIELD

The present invention is directed to methods of treating tyrosine kinase inhibitor-induced diarrhea by administering a potassium channel inhibitor, or a CFTR chloride channel inhibitor, or a combination thereof.

BACKGROUND

Diarrhea is a common, and sometimes therapy-limiting side effect caused by cancer chemotherapy. Small molecule ErbB tyrosine kinase inhibitors (TKIs) are used for the treatment of a variety of cancers that overexpress ErbB receptors including breast, non-small cell lung cancer (NSCLC), and head and neck cancers. Diarrhea associated with ErbB TKIs occurs in approximately 40-60% of patients, with severe (grades 3-4) diarrhea in 10-20% of patients. With some ErbB TKIs, diarrhea occurs in >90% of patients.

Current management of TKI-associated diarrhea includes fluid replacement, anti-motility agents such as loperamide, and in some cases TKI dose reduction or discontinuation. Given the morbidity and reduced clinical effectiveness associated with severe diarrhea following TKI therapy, there remains an unmet need for efficacious, targeted and safe antidiarrheal therapies.

SUMMARY

Aspects of the present invention are directed to methods of treating a subject with tyrosine kinase inhibitor-induced diarrhea, comprising administering to the subject an amount of a potassium channel inhibitor, or an amount of a CFTR chloride channel inhibitor, or a combination of a potassium channel inhibitor and CFTR channel inhibitor, effective to treat the tyrosine kinase inhibitor-induced diarrhea.

In addition, aspects of the present invention are also directed to methods of reducing intestinal fluid secretion resulting from tyrosine kinase inhibitor-induced activation of potassium channels or tyrosine kinase inhibitor-induced activation of CFTR chloride channels in the intestinal epithelium in a subject in need thereof, comprising administering to the subject an amount of a potassium channel inhibitor, or an amount of a CFTR chloride channel inhibitor, or an amount of combination of a potassium channel inhibitor and CFTR channel inhibitor, effective to reduce said intestinal fluid secretion.

Further aspects of the present invention are directed to methods of reducing tyrosine kinase inhibitor-induced potassium channel current or tyrosine kinase inhibitor-induced CFTR chloride channel current in the intestinal epithelium of a subject in need thereof, comprising administering to the subject an amount of a potassium channel inhibitor or an amount of a CFTR chloride channel inhibitor effective to reduce said tyrosine kinase inhibitor-induced potassium channel current or said tyrosine kinase inhibitor-induced CFTR chloride channel current.

Other aspects of the present invention are directed to an improvement to the method of treating cancer in a subject by administering to the subject an amount of a tyrosine kinase inhibitor effective to treat the subject's cancer. The improvement comprises administering a potassium channel inhibitor, or a CFTR chloride channel inhibitor, or a combination of a potassium channel inhibitor and CFTR channel inhibitor, in an amount effective to treat tyrosine kinase inhibitor-induced diarrhea in the subject.

Some aspects of the present invention are directed to a method of treating cancer in a subject, comprising administering to the subject an amount of a tyrosine kinase inhibitor effective to treat the subject's cancer; and a potassium channel inhibitor, or a CFTR chloride channel inhibitor, or a combination of a potassium channel inhibitor and CFTR chloride channel inhibitor, in an amount effective to treat tyrosine kinase inhibitor-induced diarrhea in the subject.

Finally, aspects of the present invention are directed to methods of treating diarrhea in a subject being administered a tyrosine kinase inhibitor comprising determining whether the diarrhea is tyrosine kinase inhibitor-induced diarrhea; and if said determination is that the diarrhea is tyrosine kinase inhibitor-induced diarrhea, administering to the subject an amount of a potassium channel inhibitor, or an amount of a CFTR chloride channel inhibitor, or an amount of a combination of a potassium channel inhibitor and CFTR chloride channel inhibitor, effective to treat the diarrhea.

BRIEF DESCRIPTION OF THE DRAWINGS

FIG. 3A shows the effect of BPO-27 on the carbachol-induced current in T84 cells (left), and summarizes the carbachol response as the maximum increase in short-circuit current ($\Delta Isc$)(right).

DETAILED DESCRIPTION OF ILLUSTRATIVE EMBODIMENTS

Figure 1:
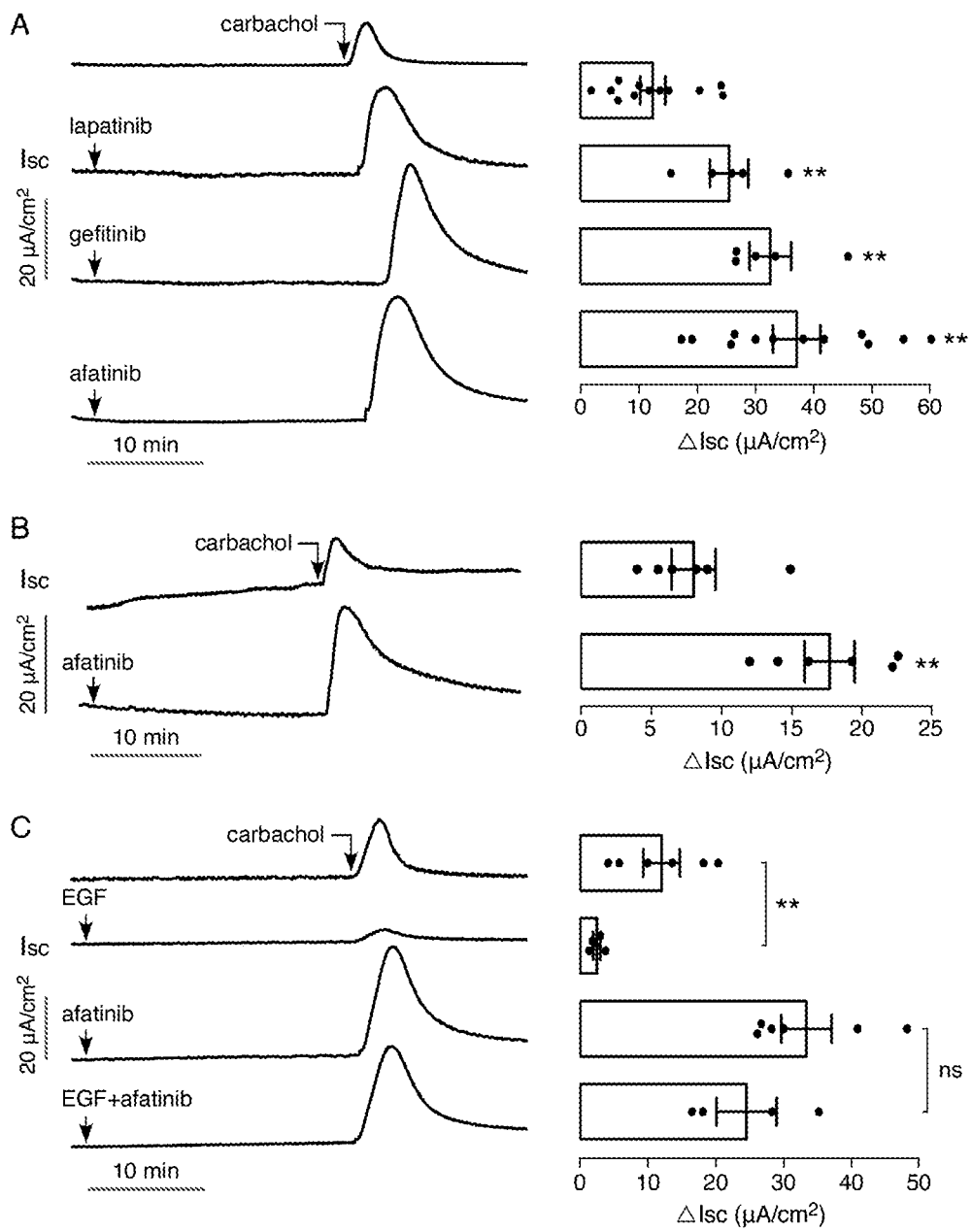
FIG. 1 shows that tyrosine kinase inhibitors amplify carbachol-induced current in T84 cells. (A) (left) Short-circuit current ($I_{sc}$) in T84 cells showing responses to 40 μM lapatinib, 20 μM gefitinib and 20 μM afatinib, added 25 min prior to 100 μM carbachol. (right) Summary of peak carbachol-induced current (mean±S.E.M.). (B) (left) Short-circuit current in mouse ileum showing responses to 20 μM afatinib added 25 min prior to 200 μM carbachol. (right) Summary of peak current ($\Delta I_{sc}$, mean±S.E.M.). (C) (left) Short-circuit current in T84 cells showing responses to 100 ng/ml EGF and 20 μM afatinib, alone and together, added 25 min prior to 100 μM carbachol. (right) Summary of peak current (mean±S.E.M.). **$p<0.01$, ns not significant.

The present invention may be understood by reference to the following detailed description which forms a part of this disclosure. The invention is not limited to the specific methods, conditions or parameters described and/or shown herein, and the terminology used herein is for the purpose of describing particular embodiments by way of example only and is not intended to be limiting of the claimed invention.

Scientific and technical terms used in connection with the present application shall have the meanings that are commonly understood by those of ordinary skill in the art, unless otherwise defined herein.

As used herein, the terms "composition," "compound," "drug," "pharmacologically active agent," "active agent," or "medicament" are used interchangeably herein to refer to a compound or compounds or composition of matter which, when administered to a subject (human or mammal) induces a desired pharmacological and/or physiologic effect by local and/or systemic action.

As used herein, the terms "treatment" or "therapy" (as well as different forms thereof) include preventative (e.g., prophylactic), curative, or palliative treatment. As used herein, the term "treating" includes alleviating or reducing at least one adverse or negative effect or symptom of a condition, disease or disorder.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to a human, to whom treatment, including prophylactic treatment, with the compounds according to the present invention, is provided.

"Pharmaceutically acceptable" refers to those compounds, materials, compositions, and/or dosage forms which are, within the scope of sound medical judgment, suitable for contact with the tissues of human beings without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These pharmaceutically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

The present invention is directed to methods of treating a subject with tyrosine kinase inhibitor-induced diarrhea, comprising administering to the subject an amount of a potassium channel inhibitor, or an amount of a CFTR chloride channel inhibitor, or a combination of a potassium channel inhibitor and CFTR channel inhibitor, effective to treat the tyrosine kinase inhibitor-induced diarrhea.

In some aspects, the present invention is directed to methods of treating a subject with tyrosine kinase inhibitor-induced diarrhea. As used herein, tyrosine kinase inhibitor-induced diarrhea refers to diarrhea experienced by a subject being administered tyrosine-kinase chemotherapy, wherein the diarrhea is caused, at least in part, by the tyrosine-kinase inhibitor administration. In some embodiments, the subject is being administered tyrosine-kinase chemotherapy as a treatment for cancer.

According to the present invention, a subject with tyrosine kinase inhibitor-induced chemotherapy is being administered a tyrosine kinase inhibitor. As used herein, a tyrosine kinase inhibitor refers to a compound that inhibits tyrosine kinases. Tyrosine kinases are enzymes that modify proteins involved in signal transduction cascades. Exemplary tyrosine kinase inhibitors are afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, and vatalanib, as well as pharmaceutically acceptable salts thereof, and combinations thereof.

In some embodiments of the methods disclosed herein, the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib, or a pharmaceutically acceptable salt thereof, or a combination thereof. In some embodiments, the tyrosine kinase inhibitor is afatinib, canertinib, cetuximab, erlotinib, gefitinib, or lapatinib, or a pharmaceutically acceptable salt thereof, or a combination thereof. In other embodiments, the tyrosine kinase inhibitor is afatinib, or a pharmaceutically acceptable salt thereof. In some aspects, the tyrosine kinase inhibitor is axitinib, or a pharmaceutically acceptable salt thereof. In some aspects, the tyrosine kinase inhibitor is bosutinib, In some aspects, the tyrosine kinase inhibitor is canertinib, or a pharmaceutically acceptable salt thereof. In some aspects, the tyrosine kinase inhibitor is crizotinib, or a pharmaceutically acceptable salt thereof. In some aspects, the tyrosine kinase inhibitor is cabozantinib, or a pharmaceutically acceptable salt thereof. In some aspects, the tyrosine kinase inhibitor is dasatinib, or a pharmaceutically acceptable salt thereof. In some aspects, the tyrosine kinase inhibitor is EKB-569, or a pharmaceutically acceptable salt thereof. In some aspects, the tyrosine kinase inhibitor is entrectinib, or a pharmaceutically acceptable salt thereof. In some aspects, the tyrosine kinase inhibitor is erlotinib, or a pharmaceutically acceptable salt thereof. In some aspects, the tyrosine kinase inhibitor is fostamatinib, or a pharmaceutically acceptable salt thereof. In some aspects, the tyrosine kinase inhibitor is gefitinib, or a pharmaceutically acceptable salt thereof. In some aspects, the tyrosine kinase inhibitor is ibrutinib, or a pharmaceutically acceptable salt thereof. In some aspects, the tyrosine kinase inhibitor is imatinib, or a pharmaceutically acceptable salt thereof. In some aspects, the tyrosine kinase inhibitor is lapatinib, or a pharmaceutically acceptable salt thereof. In some aspects, the tyrosine kinase inhibitor is leflunomide, or a pharmaceutically acceptable salt thereof. In some aspects, the tyrosine kinase inhibitor is lenvatinib, or a pharmaceutically acceptable salt thereof. In some aspects, the tyrosine kinase inhibitor is neratinib, or a pharmaceutically acceptable salt thereof. In some aspects, the tyrosine kinase inhibitor is nilotinib, or a pharmaceutically acceptable salt thereof. In some aspects, the tyrosine kinase inhibitor is pazopanib, or a pharmaceutically acceptable salt thereof. In some aspects, the tyrosine kinase inhibitor is ruxolitinib, or a pharmaceutically acceptable salt thereof. In some aspects, the tyrosine kinase inhibitor is semaxinib, or a pharmaceutically acceptable salt thereof. In some aspects, the tyrosine kinase inhibitor is sorafenib, or a pharmaceutically acceptable salt thereof. In some aspects, the tyrosine kinase inhibitor is sunitinib, or a pharmaceutically acceptable salt thereof. In some aspects, the tyrosine kinase inhibitor is SU6656, or a pharmaceutically acceptable salt thereof. In some aspects, the tyrosine kinase inhibitor is sutent, or a pharmaceutically acceptable salt thereof. In some aspects, the tyrosine kinase inhibitor is vandetanib, or a pharmaceutically acceptable salt thereof. In some aspects, the tyrosine kinase inhibitor is vatalanib, or a pharmaceutically acceptable salt thereof.

In some aspects of the methods disclosed herein, the subject is administered an amount of a potassium channel inhibitor, or an amount of a CFTR chloride channel inhibitor, or a combination of a potassium channel inhibitor and CFTR channel inhibitor, effective to treat the tyrosine kinase inhibitor-induced diarrhea.

In some embodiments, the subject is administered an amount of a potassium channel inhibitor. In other embodiments, the subject is administered an amount of a CFTR chloride channel inhibitor. In yet other embodiments, the subject is administered a combination of a potassium channel inhibitor and CFTR channel inhibitor.

As used herein, a potassium channel inhibitor refers to a compound that inhibits the passage of potassium through a potassium channel. Potassium channels are proteins that span the cell membrane and control the flow of potassium into, or out of, the cell.

There are several types of potassium channels, including calcium ($Ca^{2+}$)-activated and cAMP-activated potassium channels, which open or close in response to the presence or absence of calcium or cAMP, respectively. In some embodiments of the methods disclosed herein, the potassium channel is a $Ca^{2+}$-dependent potassium channel or a cAMP-dependent potassium channel. In some embodiments of the methods disclosed herein, the potassium channel is a $Ca^{2+}$-dependent potassium channel. In other embodiments, the potassium channel is a cAMP-dependent potassium channel.

Exemplary potassium channel inhibitors are clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, and methyl 4-[4-chloro-3-(trifluoromethyl)phenyl]-6-methyl-3-oxo-4,7-dihydro-1h-2-benzofuran-5-carboxylate.

In some embodiments of the methods disclosed herein, the subject is administered a potassium channel inhibitor that is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate; or a combination thereof.

In some embodiments, the potassium channel inhibitor is clotrimazole or senicapoc. In other embodiments, the potassium channel inhibitor is clotrimazole. In other embodiments, the potassium channel inhibitor is senicapoc. In some aspects, the potassium channel inhibitor is nitrendipine. In some aspects, the potassium channel inhibitor is 4-[[3-(trifluoromethyl)phenyl]methyl]-2h-1,4-benzothiazin-3(4h)-one. In some aspects, the potassium channel inhibitor is paxilline. In some aspects, the potassium channel inhibitor is penitrem A. In some aspects, the potassium channel inhibitor is 1-[(2-chlorophenyl)diphenylmethyl]-1h-pyrazole, 2-chloro-α,α-diphenylbenzeneacetonitrile. In some aspects, the potassium channel inhibitor is UCL 1684. In some aspects, the potassium channel inhibitor is n-trityl-3-pyridinemethanamine. In some aspects, the potassium channel inhibitor is methyl 4-[4-chloro-3-(trifluoromethyl)phenyl]-6-methyl-3-oxo-4,7-dihydro-1h-2-benzofuran-5-carboxylate. Other potassium channels are known in the art, and could also be used in these embodiments.

The amount of the potassium channel inhibitor administered is an amount that is effective to treat the tyrosine kinase inhibitor-induced diarrhea. The amount that is effective in this regard will vary depending on the subject's characteristics and condition.

In some aspects of the methods disclosed herein, the subject is administered an amount of a CFTR chloride channel inhibitor. As used herein, a CFTR chloride channel refers to the Cystic Fibrosis Transmembrane Conductance Regulator (CFTR), a cAMP-activated chloride channel expressed in epithelia in the lung, intestine, pancreas, testis and other tissues. A CFTR chloride channel inhibitor is a compound that inhibits the passage of chloride through the CFTR chloride channel.

Exemplary CFTR chloride channel inhibitors include (R)—BPO-27, $CFTR_{inh}$-172, GlyH-101, glibenclamide, diphenylamine-2-carboxylate, 5-nitro-2-(3-phenylpropylamino) benzoate, and niflumic acid.

In some embodiments of the methods disclosed herein, the subject is administered (R)—BPO-27, $CFTR_{inh}$-172, GlyH-101, glibenclamide, diphenylamine-2-carboxylate, 5-nitro-2-(3-phenylpropylamino) benzoate, or niflumic acid; or a combination thereof.

In some embodiments, the CFTR chloride channel inhibitor is (R)—BPO-27, a compound having the structure:

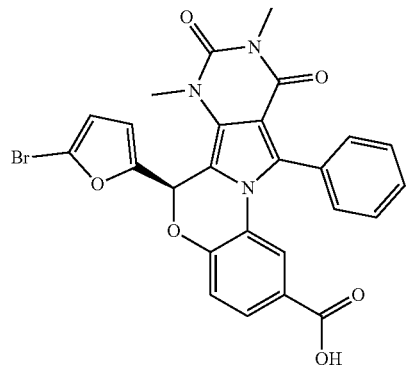

In some embodiments, the CFTR chloride channel inhibitor is $CFTR_{inh}$-172. In some embodiments, the CFTR chloride channel inhibitor is GlyH-101. In some embodiments, the CFTR chloride channel inhibitor is glibenclamide. In some embodiments, the CFTR chloride channel inhibitor is diphenylamine-2-carboxylate. In some embodiments, the CFTR chloride channel inhibitor is 5-nitro-2-(3-phenylpropylamino) benzoate. In some embodiments, the CFTR chloride channel inhibitor is niflumic acid.

In some embodiments, the subject is administered a pharmaceutical composition comprising a pharmaceutical excipient and an amount of a potassium channel inhibitor. In other embodiments, the subject is administered a pharmaceutical composition comprising a pharmaceutical excipient and an amount of a CFTR chloride channel inhibitor. In yet other embodiments, the subject is administered a pharmaceutical composition comprising a pharmaceutical excipient, a potassium channel inhibitor, and a CFTR channel inhibitor.

In those embodiments wherein the subject is administered a pharmaceutical composition comprising a CFTR chloride channel inhibitor that is (R)—BPO-27, the pharmaceutical composition may also include (S)—BPO-27. In these embodiments, the amount of (R)—BPO-27 in the pharmaceutical composition will be substantially equal to, or more than, the amount of (S)—BPO-27 present in the pharmaceutical composition. For example, in some embodiments, the pharmaceutical composition may include a racemic mixture of (R/S)—BPO-27. In some aspects, the (R)—BPO-27 will be present in an enantiomeric excess (ee), as compared to the (S)—BPO-27. For example, the (R)—BPO-27 can be present in about a 1, 2, 3, 4, 5, 6, 7, 8, 9, 10, 15, 20, 25, 30, 35, 40, 45, 50, 55, 60, 65, 70, 75, 80, 85, 90, 95, or 99% ee. In some embodiments, the pharmaceutical composition will include (R)—BPO-27 wherein the % ee is greater than 99%.

The amount of CFTR chloride channel inhibitor administered is an amount that is effective to treat the tyrosine kinase inhibitor-induced diarrhea. The amount that is effective in this regard will vary depending on the subject's characteristics and condition.

In some aspects of the methods disclosed herein, the subject is administered a combination of an amount of a potassium channel inhibitor, and an amount of a CFTR chloride channel inhibitor. In some embodiments in which the subject is administered a combination of a potassium channel inhibitor and a CFTR chloride channel inhibitor, the potassium channel inhibitor is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate; and the CFTR chloride channel inhibitor is (R)—BPO-27, $CFTR_{inh}$-172, GlyH-101, glibenclamide, diphenylamine-2-carboxylate, 5-nitro-2-(3-phenylpropylamino) benzoate, or niflumic acid.

In some embodiments, the potassium channel inhibitor is clotrimazole or senicapoc, and the CFTR chloride channel inhibitor is (R)—BPO-27. In some embodiments, the potassium channel inhibitor is clotrimazole or senicapoc, and the CFTR chloride channel inhibitor is $CFTR_{inh}$-172. In some embodiments, the potassium channel inhibitor is clotrimazole or senicapoc, and the CFTR chloride channel inhibitor is GlyH-101. In some embodiments, the potassium channel inhibitor is clotrimazole or senicapoc, and the CFTR chloride channel inhibitor is glibenclamide. In some embodiments, the potassium channel inhibitor is clotrimazole or senicapoc, and the CFTR chloride channel inhibitor is diphenylamine-2-carboxylate. In some embodiments, the potassium channel inhibitor is clotrimazole or senicapoc, and the CFTR chloride channel inhibitor is 5-nitro-2-(3-phenylpropylamino) benzoate. In some embodiments, the potassium channel inhibitor is clotrimazole or senicapoc, and the CFTR chloride channel inhibitor is niflumic acid.

In some aspects, the present invention is directed to methods of reducing intestinal fluid secretion resulting from tyrosine kinase inhibitor-induced activation of potassium channels or tyrosine kinase inhibitor-induced activation of CFTR chloride channels in the intestinal epithelium in a subject in need thereof, comprising administering to the subject an amount of a potassium channel inhibitor, or an amount of a CFTR chloride channel inhibitor; or an amount of combination of a potassium channel inhibitor and CFTR channel inhibitor, effective to reduce said intestinal fluid secretion.

As used herein, intestinal fluid secretion refers to secretion of fluid from the intestinal epithelia into the intestinal lumen.

In some embodiments, the intestinal fluid secretion results from tyrosine kinase inhibitor-induced activation of potassium channels in the intestinal epithelium. In some embodiments, the potassium channels are basolateral potassium channels. Basolateral potassium channels are potassium channels on the basolateral cell membrane (i.e., the cell membrane facing the extracellular fluid).

In some embodiments, the intestinal fluid secretion results from tyrosine kinase inhibitor-induced activation of CFTR chloride channels in the intestinal epithelium. In other embodiments, the CFTR chloride channels are apical CFTR chloride channels in the intestinal epithelium. Apical CFTR chloride channels are CFTR chloride channels located in the apical cell membrane (i.e., the cell membrane facing the intestinal lumen).

In some embodiments, the tyrosine kinase inhibitor-induced activation of potassium channels, or the tyrosine kinase inhibitor-induced activation of CFTR chloride channels in the intestinal epithelium is induced by a tyrosine kinase inhibitor such as, for example, afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof.

In some embodiments, the tyrosine kinase inhibitor-induced activation of potassium channels, or the tyrosine kinase inhibitor-induced activation of CFTR chloride channels in the intestinal epithelium is induced by a tyrosine kinase inhibitor that is afatinib, canertinib, cetuximab, erlotinib, gefitinib, or lapatinib; or a pharmaceutically acceptable salt thereof. In some embodiments, the tyrosine kinase inhibitor is afatinib, or a pharmaceutically acceptable salt thereof. In some aspects, the tyrosine kinase inhibitor is axitinib, or a pharmaceutically acceptable salt thereof. In some aspects, the tyrosine kinase inhibitor is bosutinib, In some aspects, the tyrosine kinase inhibitor is canertinib, or a pharmaceutically acceptable salt thereof. In some aspects, the tyrosine kinase inhibitor is crizotinib, or a pharmaceutically acceptable salt thereof. In some aspects, the tyrosine kinase inhibitor is cabozantinib, or a pharmaceutically acceptable salt thereof. In some aspects, the tyrosine kinase inhibitor is EKB-569, or a pharmaceutically acceptable salt thereof. In some aspects, the tyrosine kinase inhibitor is dasatinib, or a pharmaceutically acceptable salt thereof. In some aspects, the tyrosine kinase inhibitor is entrectinib, or a pharmaceutically acceptable salt thereof. In some aspects, the tyrosine kinase inhibitor is erlotinib, or a pharmaceutically acceptable salt thereof. In some aspects, the tyrosine kinase inhibitor is fostamatinib, or a pharmaceutically acceptable salt thereof. In some aspects, the tyrosine kinase inhibitor is gefitinib, or a pharmaceutically acceptable salt thereof. In some aspects, the tyrosine kinase inhibitor is ibrutinib, or a pharmaceutically acceptable salt thereof. In some aspects, the tyrosine kinase inhibitor is imatinib, or a pharmaceutically acceptable salt thereof. In some aspects, the tyrosine kinase inhibitor is lapatinib, or a pharmaceutically acceptable salt thereof. In some aspects, the tyrosine kinase inhibitor is leflunomide, or a pharmaceutically acceptable salt thereof. In some aspects, the tyrosine kinase inhibitor is lenvatinib, or a pharmaceutically acceptable salt thereof. In some aspects, the tyrosine kinase inhibitor is neratinib, or a pharmaceutically acceptable salt thereof. In some aspects, the tyrosine kinase inhibitor is nilotinib, or a pharmaceutically acceptable salt thereof. In some aspects, the tyrosine kinase inhibitor is pazopanib, or a pharmaceutically acceptable salt thereof. In some aspects, the tyrosine kinase inhibitor is ruxolitinib, or a pharmaceutically acceptable salt thereof. In some aspects, the tyrosine kinase inhibitor is semaxinib, or a pharmaceutically acceptable salt thereof. In some aspects, the tyrosine kinase inhibitor is sorafenib, or a pharmaceutically acceptable salt thereof. In some aspects, the tyrosine kinase inhibitor is sunitinib, or a pharmaceutically acceptable salt thereof. In some aspects, the tyrosine kinase inhibitor is SU6656, or a pharmaceutically acceptable salt thereof. In some aspects, the tyrosine kinase inhibitor is sutent, or a pharmaceutically acceptable salt thereof. In some aspects, the tyrosine kinase inhibitor is vandetanib, or a pharmaceutically acceptable salt thereof. In some aspects, the tyrosine kinase inhibitor is vatalanib, or a pharmaceutically acceptable salt thereof.

In some aspects, the intestinal fluid secretion is reduced by administering an amount of a potassium channel inhibitor, or an amount of a CFTR chloride channel inhibitor; or an amount of combination of a potassium channel inhibitor and CFTR channel inhibitor, effective to reduce said intestinal fluid secretion. As used herein, reduction of intestinal fluid secretion refers to a decrease in the amount of fluid that is secreted into the intestinal lumen relative to the amount of fluid that is secreted into the intestinal lumen in the absence of administration of a potassium channel inhibitor and/or a CFTR chloride channel inhibitor. Methods of measuring decrease in fluid secretion are known to those skilled in the art, and include measuring the water content of the intestinal luminal contents, and diarrhea output.

In some embodiments, the intestinal fluid secretion is reduced by administering a potassium channel inhibitor that is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof. In some embodiments, the potassium channel inhibitor is clotrimazole or senicapoc. In other embodiments, the potassium channel inhibitor is clotrimazole. In other embodiments, the potassium channel inhibitor is senicapoc. In some aspects, the potassium channel inhibitor is nitrendipine. In some aspects, the potassium channel inhibitor is 4-[[3-(trifluoromethyl)phenyl]methyl]-2h-1,4-benzothiazin-3(4h)-one. In some aspects, the potassium channel inhibitor is paxilline. In some aspects, the potassium channel inhibitor is penitrem A. In some aspects, the potassium channel inhibitor is 1-[(2-chlorophenyl)diphenylmethyl]-1h-pyrazole, 2-chloro-α,α-diphenylbenzeneacetonitrile. In some aspects, the potassium channel inhibitor is UCL 1684. In some aspects, the potassium channel inhibitor is n-trityl-3-pyridinemethanamine. In some aspects, the potassium channel inhibitor is methyl 4-[4-chloro-3-(trifluoromethyl)phenyl]-6-methyl-3-oxo-4,7-dihydro-1h-2-benzofuran-5-carboxylate. Other potassium channels are known in the art, and can be used in certain embodiments.

In some embodiments, the intestinal fluid secretion is reduced by administering a CFTR chloride channel inhibitor that is (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof. In some embodiments, the CFTR chloride channel inhibitor is (R)—BPO-27. In some embodiments, the CFTR chloride channel inhibitor is $CFTR_{inh}$-172. In some embodiments, the CFTR chloride channel inhibitor is GlyH-101. In some embodiments, the CFTR chloride channel inhibitor is glibenclamide. In some embodiments, the CFTR chloride channel inhibitor is diphenylamine-2-carboxylate. In some embodiments, the CFTR chloride channel inhibitor is 5-nitro-2-(3-phenylpropylamino) benzoate. In some embodiments, the CFTR chloride channel inhibitor is niflumic acid.

In some aspects, the present invention is directed to methods of reducing tyrosine kinase inhibitor-induced potassium channel current or tyrosine kinase inhibitor-induced CFTR chloride channel current in the intestinal epithelium of a subject in need thereof, comprising administering to the subject an amount of a potassium channel inhibitor, or an amount of a CFTR chloride channel inhibitor, or an amount of combination of a potassium channel inhibitor and CFTR channel inhibitor, effective to reduce said tyrosine kinase inhibitor-induced potassium channel current or tyrosine kinase inhibitor-induced CFTR chloride channel current.

In some embodiments, the present invention is directed to methods of reducing tyrosine-kinase inhibitor induced potassium channel current in the intestinal epithelium. In other embodiments, the present invention is directed to methods of reducing tyrosine-kinase inhibitor-induced CFTR chloride channel current in the intestinal epithelium. In other embodiments, the present invention is directed to methods of reducing tyrosine-kinase inhibitor induced potassium channel current and tyrosine-kinase inhibitor-induced CFTR chloride channel current, in the intestinal epithelium.

As used here, "current" refers to the passage of ions through the channel. Thus, potassium channel current refers to the passage of potassium ions through the potassium channel, and CFTR chloride channel current refers to the passage of chloride ions through the CFTR chloride channel.

In some embodiments, the tyrosine kinase inhibitor-induced potassium channel current or tyrosine kinase inhibitor-induced CFTR chloride channel current in the intestinal epithelium is induced by a tyrosine kinase inhibitor that is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof. In some embodiments, the tyrosine kinase inhibitor is afatinib, canertinib, cetuximab, erlotinib, gefitinib, or lapatinib; or a pharmaceutically acceptable salt thereof. In some embodiments, the tyrosine kinase inhibitor is afatinib. In some aspects, the tyrosine kinase inhibitor is axitinib, or a pharmaceutically acceptable salt thereof. In some aspects, the tyrosine kinase inhibitor is bosutinib, In some aspects, the tyrosine kinase inhibitor is canertinib, or a pharmaceutically acceptable salt thereof. In some aspects, the tyrosine kinase inhibitor is crizotinib, or a pharmaceutically acceptable salt thereof. In some aspects, the tyrosine kinase inhibitor is cabozantinib, or a pharmaceutically acceptable salt thereof. In some aspects, the tyrosine kinase inhibitor is EKB-569, or a pharmaceutically acceptable salt thereof. In some aspects, the tyrosine kinase inhibitor is dasatinib, or a pharmaceutically acceptable salt thereof. In some aspects, the tyrosine kinase inhibitor is entrectinib, or a pharmaceutically acceptable salt thereof. In some aspects, the tyrosine kinase inhibitor is erlotinib, or a pharmaceutically acceptable salt thereof. In some aspects, the tyrosine kinase inhibitor is fostamatinib, or a pharmaceutically acceptable salt thereof. In some aspects, the tyrosine kinase inhibitor is gefitinib, or a pharmaceutically acceptable salt thereof. In some aspects, the tyrosine kinase inhibitor is ibrutinib, or a pharmaceutically acceptable salt thereof. In some aspects, the tyrosine kinase inhibitor is imatinib, or a pharmaceutically acceptable salt thereof. In some aspects, the tyrosine kinase inhibitor is lapatinib, or a pharmaceutically acceptable salt thereof. In some aspects, the tyrosine kinase inhibitor is leflunomide, or a pharmaceutically acceptable salt thereof. In some aspects, the tyrosine kinase inhibitor is lenvatinib, or a pharmaceutically acceptable salt thereof. In some aspects, the tyrosine kinase inhibitor is neratinib, or a pharmaceutically acceptable salt thereof. In some aspects, the tyrosine kinase inhibitor is nilotinib, or a pharmaceutically acceptable salt thereof. In some aspects, the tyrosine kinase inhibitor is pazopanib, or a pharmaceutically acceptable salt thereof. In some aspects, the tyrosine kinase inhibitor is ruxolitinib, or a pharmaceutically acceptable salt thereof. In some aspects, the tyrosine kinase inhibitor is semaxinib, or a pharmaceutically acceptable salt thereof. In some aspects, the tyrosine kinase inhibitor is sorafenib, or a pharmaceutically acceptable salt thereof. In some aspects, the tyrosine kinase inhibitor is sunitinib, or a pharmaceutically acceptable salt thereof. In some aspects, the tyrosine kinase inhibitor is SU6656, or a pharmaceutically acceptable salt thereof. In some aspects, the tyrosine kinase inhibitor is sutent, or a pharmaceutically acceptable salt thereof. In some aspects, the tyrosine kinase inhibitor is vandetanib, or a pharmaceutically acceptable salt thereof. In some aspects, the tyrosine kinase inhibitor is vatalanib, or a pharmaceutically acceptable salt thereof.

In some embodiments, the tyrosine kinase inhibitor-induced potassium channel current in the intestinal epithelium is reduced by administering a potassium channel inhibitor such as, for example, clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof. In some embodiments, the potassium channel inhibitor is clotrimazole or senicapoc. In other embodiments, the potassium channel inhibitor is clotrimazole. In other embodiments, the potassium channel inhibitor is senicapoc. In some aspects, the potassium channel inhibitor is nitrendipine. In some aspects, the potassium channel inhibitor is 4-[[3-(trifluoromethyl)phenyl]methyl]-2h-1,4-benzothiazin-3(4h)-one. In some aspects, the potassium channel inhibitor is paxilline. In some aspects, the potassium channel inhibitor is penitrem A. In some aspects, the potassium channel inhibitor is 1-[(2-chlorophenyl)diphenylmethyl]-1h-pyrazole, 2-chloro-α,α-diphenylbenzeneacetonitrile. In some aspects, the potassium channel inhibitor is UCL 1684. In some aspects, the potassium channel inhibitor is n-trityl-3-pyridinemethanamine. In some aspects, the potassium channel inhibitor is methyl 4-[4-chloro-3-(trifluoromethyl)phenyl]-6-methyl-3-oxo-4,7-dihydro-1h-2-benzofuran-5-carboxylate.

In some embodiments, the tyrosine kinase inhibitor-induced CFTR chloride channel current in the intestinal epithelium is reduced by administering a CFTR chloride channel inhibitor that is (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof. In some embodiments, the CFTR chloride channel inhibitor is (R)—BPO-27. In some embodiments, the CFTR chloride channel inhibitor is $CFTR_{inh}$-172. In some embodiments, the CFTR chloride channel inhibitor is GlyH-101. In some embodiments, the CFTR chloride channel inhibitor is glibenclamide. In some embodiments, the CFTR chloride channel inhibitor is diphenylamine-2-carboxylate. In some embodiments, the CFTR chloride channel inhibitor is 5-nitro-2-(3-phenylpropylamino) benzoate. In some embodiments, the CFTR chloride channel inhibitor is niflumic acid.

In some aspects, the present invention is directed to methods of treating cancer in a subject by administering to the subject an amount of a tyrosine kinase inhibitor effective to treat the subject's cancer; and a potassium channel inhibitor, or a CFTR chloride channel inhibitor, or a combination of a potassium channel inhibitor and CFTR chloride channel inhibitor, in an amount effective to treat tyrosine kinase inhibitor-induced diarrhea in the subject. As such, the present invention, in a method of treating cancer in a subject consisting essentially of administering to the subject an amount of a tyrosine kinase inhibitor effective to treat the subject's cancer, provides an improvement in such treatment that comprises administering a potassium channel inhibitor, or a CFTR chloride channel inhibitor, or a combination of a potassium channel inhibitor and CFTR chloride channel inhibitor, in an amount effective to treat tyrosine kinase inhibitor-induced diarrhea in the subject.

In some embodiments, the cancer is adenoid cystic carcinoma, adrenal gland tumor, anal cancer, bile duct cancer, bladder cancer, bone cancer, brain tumor, breast cancer, breast cancer in men, carcinoid tumor, cervical cancer, colorectal cancer, ductal carcinoma, endometrial cancer, esophageal cancer, gastric cancer, gastrointestinal stromal tumor—GIST, HER2-positive breast cancer, kidney cancer, laryngeal cancer, leukemia, liver cancer, lobular carcinoma, lung cancer, non-small cell lung cancer (NSCLC), head and neck cancers, Hodgkin's lymphoma, non-Hodgkin's lymphoma, malignant glioma, melanoma, meningioma, multiple endocrine neoplasia type 1, multiple endocrine neoplasia type 2, multiple myeloma, nasopharyngeal cancer, neuroendocrine tumor, nevoid basal cell carcinoma syndrome, oral cancer, osteosarcoma, ovarian cancer, pancreatic cancer, pancreatic neuroendocrine tumors, parathyroid cancer, penile cancer, peritoneal cancer, pituitary gland tumor, prostate cancer, renal cell cancer, retinoblastoma, salivary gland cancer, sarcoma, skin cancer (non-melanoma), small bowel cancer, stomach cancer, testicular cancer, thyroid cancer, uterine (endometrial) cancer, or vaginal cancer.

In some embodiments, the cancer is gastrointestinal stromal tumors, chronic myeloid leukemia, chronic myelomonocytic leukemia, chronic eosinophilic leukemia, non-small cell lung cancer, heptocellular cancer, pancreatic cancer, renal cancer, breast cancer, colorectal cancer, ovarian cancer, melanoma, prostate cancer, squamous cell carcinoma, or kidney cancer.

In some embodiments, the subject has a mutation in a gene encoding an ErbB family member. The ErbB gene can encode epidermal growth factor receptor (EGFR). In some embodiments, the EGFR comprises a mutation is in exon 18 (see Kobayashi et al. *Clin. Cancer Res.* 21:5305-5313, 2015, which is hereby incorporated by reference in entirety). In certain embodiments, the mutation is in the codon encoding the amino acid at position E709, G719, or a combination thereof. For example, the mutation can be in the codon encoding E709K, E709A, E709G, E709V, E709H, G719A, G719S, G719C, G719D, G719V, or a combination thereof.

In certain embodiments, the mutation is an exon 18 deletion. For example, the exon 18 deletion may be DelE709_T710insD.

In some aspects of the methods disclosed herein, the subject is administered an amount of a tyrosine kinase inhibitor effective to treat the subject's cancer. The amount of tyrosine kinase inhibitor that is effective in this regard will vary depending on the tyrosine kinase inhibitor, as well as the subject's characteristics and condition.

In some embodiments of the methods of treating cancer, the tyrosine kinase inhibitor administered to the subject is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof. In some embodiments of the methods of treating cancer, the tyrosine kinase inhibitor is afatinib, canertinib, cetuximab, erlotinib, gefitinib, or lapatinib; or a pharmaceutically acceptable salt thereof. In some embodiments of the methods of treating cancer, the tyrosine kinase inhibitor is afatinib, or a pharmaceutically acceptable salt thereof. In some aspects, the tyrosine kinase inhibitor is axitinib, or a pharmaceutically acceptable salt thereof. In some aspects, the tyrosine kinase inhibitor is bosutinib, In some aspects, the tyrosine kinase inhibitor is canertinib, or a pharmaceutically acceptable salt thereof. In some aspects, the tyrosine kinase inhibitor is crizotinib, or a pharmaceutically acceptable salt thereof. In some aspects, the tyrosine kinase inhibitor is cabozantinib, or a pharmaceutically acceptable salt thereof. In some aspects, the tyrosine kinase inhibitor is EKB-569, or a pharmaceutically acceptable salt thereof. In some aspects, the tyrosine kinase inhibitor is dasatinib, or a pharmaceutically acceptable salt thereof. In some aspects, the tyrosine kinase inhibitor is entrectinib, or a pharmaceutically acceptable salt thereof. In some aspects, the tyrosine kinase inhibitor is erlotinib, or a pharmaceutically acceptable salt thereof. In some aspects, the tyrosine kinase inhibitor is fostamatinib, or a pharmaceutically acceptable salt thereof. In some aspects, the tyrosine kinase inhibitor is gefitinib, or a pharmaceutically acceptable salt thereof. In some aspects, the tyrosine kinase inhibitor is ibrutinib, or a pharmaceutically acceptable salt thereof. In some aspects, the tyrosine kinase inhibitor is imatinib, or a pharmaceutically acceptable salt thereof. In some aspects, the tyrosine kinase inhibitor is lapatinib, or a pharmaceutically acceptable salt thereof. In some aspects, the tyrosine kinase inhibitor is leflunomide, or a pharmaceutically acceptable salt thereof. In some aspects, the tyrosine kinase inhibitor is lenvatinib, or a pharmaceutically acceptable salt thereof. In some aspects, the tyrosine kinase inhibitor is neratinib, or a pharmaceutically acceptable salt thereof. In some aspects, the tyrosine kinase inhibitor is nilotinib, or a pharmaceutically acceptable salt thereof. In some aspects, the tyrosine kinase inhibitor is pazopanib, or a pharmaceutically acceptable salt thereof. In some aspects, the tyrosine kinase inhibitor is ruxolitinib, or a pharmaceutically acceptable salt thereof. In some aspects, the tyrosine kinase inhibitor is semaxinib, or a pharmaceutically acceptable salt thereof. In some aspects, the tyrosine kinase inhibitor is sorafenib, or a pharmaceutically acceptable salt thereof. In some aspects, the tyrosine kinase inhibitor is sunitinib, or a pharmaceutically acceptable salt thereof. In some aspects, the tyrosine kinase inhibitor is SU6656, or a pharmaceutically acceptable salt thereof. In some aspects, the tyrosine kinase inhibitor is sutent, or a pharmaceutically acceptable salt thereof. In some aspects, the tyrosine kinase inhibitor is vandetanib, or a pharmaceutically acceptable salt thereof. In some aspects, the tyrosine kinase inhibitor is vatalanib, or a pharmaceutically acceptable salt thereof.

In some aspects of the methods of treating cancer, the subject is administered a potassium channel inhibitor, or a CFTR chloride channel inhibitor, or a combination of a potassium channel inhibitor and CFTR chloride channel inhibitor, in an amount effective to treat tyrosine kinase inhibitor-induced diarrhea in the subject.

In some embodiments, the subject is administered a potassium channel inhibitor such as, for example, clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof. In some embodiments, the potassium channel inhibitor is clotrimazole or senicapoc. In other embodiments, the potassium channel inhibitor is clotrimazole. In other embodiments, the potassium channel inhibitor is senicapoc. In some aspects, the potassium channel inhibitor is nitrendipine. In some aspects, the potassium channel inhibitor is 4-[[3-(trifluoromethyl)phenyl]methyl]-2h-1,4-benzothiazin-3(4h)-one. In some aspects, the potassium channel inhibitor is paxilline. In some aspects, the potassium channel inhibitor is penitrem A. In some aspects, the potassium channel inhibitor is 1-[(2-chlorophenyl)diphenylmethyl]-1h-pyrazole, 2-chloro-α,α-diphenylbenzeneacetonitrile. In some aspects, the potassium channel inhibitor is UCL 1684. In some aspects, the potassium channel inhibitor is n-trityl-3-pyridinemethanamine. In some aspects, the potassium channel inhibitor is methyl 4-[4-chloro-3-(trifluoromethyl)phenyl]-6-methyl-3-oxo-4,7-dihydro-1h-2-benzofuran-5-carboxylate.

The amount of the potassium channel inhibitor administered is an amount that is effective to treat the tyrosine kinase inhibitor-induced diarrhea. The amount that is effective in this regard will vary depending on the subject's characteristics and condition.

In some embodiments, the subject is administered a CFTR chloride channel inhibitor such as, for example, (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof. In some embodiments, the CFTR chloride channel inhibitor is (R)—BPO-27. In some embodiments, the CFTR chloride channel inhibitor is $CFTR_{inh}$-172. In some embodiments, the CFTR chloride channel inhibitor is GlyH-101. In some embodiments, the CFTR chloride channel inhibitor is glibenclamide. In some embodiments, the CFTR chloride channel inhibitor is diphenylamine-2-carboxylate. In some embodiments, the CFTR chloride channel inhibitor is 5-nitro-2-(3-phenylpropylamino) benzoate. In some embodiments, the CFTR chloride channel inhibitor is niflumic acid.

The amount of the CFTR chloride channel inhibitor administered is an amount that is effective to treat the tyrosine kinase inhibitor-induced diarrhea. The amount that is effective in this regard will vary depending on the subject's characteristics and condition.

In some embodiments, the subject is administered a combination of a potassium channel inhibitor and a CFTR chloride channel inhibitor. The amount of the combination of a potassium channel inhibitor and a CFTR chloride channel inhibitor administered is an amount that is effective to treat the tyrosine kinase inhibitor-induced diarrhea. The amount that is effective in this regard will vary depending on the subject's characteristics and condition.

In some aspects, the present invention is directed to methods of treating diarrhea in a subject being administered a tyrosine kinase inhibitor comprising (1) determining whether the diarrhea is tyrosine kinase inhibitor-induced diarrhea; and (2) if said determination is that the diarrhea is tyrosine kinase inhibitor-induced diarrhea, administering to the subject an amount of a potassium channel inhibitor, or an amount of a CFTR chloride channel inhibitor, or an amount of or a combination of a potassium channel inhibitor and CFTR chloride channel inhibitor, effective to treat the diarrhea.

In this aspect, the methods comprise determining whether the diarrhea is tyrosine kinase inhibitor-induced diarrhea. Methods for determining whether diarrhea is tyrosine kinase induced diarrhea are known to persons skilled in the art, and include, for example, assessing whether or not the subject is undergoing tyrosine kinase inhibitor therapy, such as, for example, by questioning the subject. In other aspects, the assessment requires assessing the subject's medical history, assessing the subject's diet, and assessing whether the subject has contracted a bacterial or viral infection. Methods of determining whether the diarrhea is tyrosine kinase inhibitor-induced also include the exclusion of any other cause for the diarrhea.

In the methods of this aspect, if the subject's diarrhea is determined to be tyrosine kinase-induced diarrhea, then the subject is administered an amount of a potassium channel inhibitor, or an amount of a CFTR chloride channel inhibitor, or an amount of or a combination of a potassium channel inhibitor and CFTR chloride channel inhibitor, effective to treat the diarrhea.

In some embodiments of this aspect, the subject is administered a potassium channel inhibitor such as, for example, clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof. In some embodiments, the potassium channel inhibitor is clotrimazole or senicapoc. In other embodiments, the potassium channel inhibitor is clotrimazole. In other embodiments, the potassium channel inhibitor is senicapoc. In some aspects, the potassium channel inhibitor is nitrendipine. In some aspects, the potassium channel inhibitor is 4-[[3-(trifluoromethyl)phenyl]methyl]-2h-1,4-benzothiazin-3(4h)-one. In some aspects, the potassium channel inhibitor is paxilline. In some aspects, the potassium channel inhibitor is penitrem A. In some aspects, the potassium channel inhibitor is 1-[(2-chlorophenyl)diphenylmethyl]-1h-pyrazole, 2-chloro-α,α-diphenylbenzeneacetonitrile. In some aspects, the potassium channel inhibitor is UCL 1684. In some aspects, the potassium channel inhibitor is n-trityl-3-pyridinemethanamine. In some aspects, the potassium channel inhibitor is methyl 4-[4-chloro-3-(trifluoromethyl) phenyl]-6-methyl-3-oxo-4,7-dihydro-1h-2-benzofuran-5-carboxylate.

The amount of the potassium channel inhibitor administered is an amount that is effective to treat the tyrosine kinase inhibitor-induced diarrhea. The amount that is effective in this regard will vary depending on the subject's characteristics and condition.

In other embodiments of this aspect, the subject is administered a CFTR chloride channel inhibitor such as, for example, (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof. In some embodiments, the CFTR chloride channel inhibitor is (R)—BPO-27. In some embodiments, the CFTR chloride channel inhibitor is $CFTR_{inh}$-172. In some embodiments, the CFTR chloride channel inhibitor is GlyH-101. In some embodiments, the CFTR chloride channel inhibitor is glibenclamide. In some embodiments, the CFTR chloride channel inhibitor is diphenylamine-2-carboxylate. In some embodiments, the CFTR chloride channel inhibitor is 5-nitro-2-(3-phenylpropylamino) benzoate. In some embodiments, the CFTR chloride channel inhibitor is niflumic acid.

The amount of the CFTR chloride channel inhibitor administered is an amount that is effective to treat the tyrosine kinase inhibitor-induced diarrhea. The amount that is effective in this regard will vary depending on the subject's characteristics and condition.

In some embodiments of this aspect, the subject is administered an amount of or a combination of a potassium channel inhibitor and CFTR chloride channel inhibitor effective to treat the tyrosine kinase inhibitor-induced diarrhea. The amount that is effective in this regard will vary depending on the subject's characteristics and condition.

EXAMPLES

The following examples are provided to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the scope of the present invention.

Abbreviations

BAPTA—1,2-bis(o-aminophenoxy)ethane-N,N,N',N'-tetraacetic acid
EGF—Epidermal growth factor
ERK—extracellular signal-regulated kinase
PKC—Protein kinase C Chemicals Lapatinib and gefitinib are purchased from Synkinase (San Diego, CA), and afatinib from Abcam (Cambridge, MA). BAPTA-AM is purchased from EMD Millipore (Billerica, MA). Clotrimazole is purchased from Spectrum Chemicals (Gardena, CA) and senicapoc from MedChem Express (Monmouth Junction, NJ). PKC inhibitor Ro 31-8220 is purchased from TOCRIS Bioscience (Bristol, UK) and ERK inhibitor GDC-0994 from APExBIO (Boston, MA). EGF and thapsigargin is purchased from Abcam (Cambridge, MA). Forskolin, carbachol and other chemicals are purchased from Sigma-Aldrich (St. Louis, MO). CFTRinh-172 and (R)—BPO-27 (herein called BPO-27) are synthesized and purified as described in Snyder D S, Tradtrantip L, Yao C, Kurth M J, and Verkman A S. Potent, metabolically stable benzopyrimido-pyrrolo-oxazine-dione (BPO) CFTR inhibitors for polycystic kidney disease. *J Med Chem.* 2011; 54(15):5468-77; Snyder D S, Tradtrantip L, Battula S, Yao C, Phuan P W, Fettinger J C, et al. Absolute configuration and biological properties of enantiomers of CFTR inhibitor BPO-27. *ACS Med Chem Lett.* 2013; 4(5):

456-9; Ma T, Thiagarajah J R, Yang H, Sonawane N D, Folli C, Galietta L J, et al. Thiazolidinone CFTR inhibitor identified by high-throughput screening blocks cholera toxin-induced intestinal fluid secretion. *J Clin Invest.* 2002; 110 (11):1651-8.

Cell Culture

T84 cells (ATCC CCL-248) are cultured in a 1:1 mixture of DMEM/Ham's F-12 medium supplemented with 10% FBS, 100 U/mL penicillin and 100 µg/mL streptomycin. Cells are grown on Snapwell inserts (Costar Corning, Horseheads, NY) at 37° C. in 5% $CO_2$/95% air and used 7-10 days after plating.

Short-Circuit Current Measurement

T84 cells are mounted in Ussing chambers and bathed in symmetrical $HCO_3$-buffered solution containing (in mM): 120 NaCl, 5 KCl, 1 $MgCl_2$, 1 $CaCl_2$, 10 D-glucose, 5 HEPES and 25 $NaHCO_3$ (pH 7.4). The solutions are aerated with 95% O2/5% $CO_2$ and maintained at 37° C. For measurement of basolateral $K^+$ conductance, a mucosal-to-serosal $K^+$ gradient is established using solutions containing $K^+$ as the major charge-carrying ion. The apical solution contained (in mM): 142.5 K-gluconate, 1.25 $CaCl_2$, 0.40 $MgSO_4$, 0.43 $KH_2PO_4$, 0.35 $Na_2HPO_4$, 10 HEPES, 5.6 D-glucose, pH 7.4. In basolateral solution 142.5 mM K-gluconate is replaced by 5.4 mM K-gluconate and 136.9 mM N-methylglucamine, and the apical membrane is permeabilized with 20 µM amphotericin B (Rufo P A, Merlin D, Riegler M, Ferguson-Maltzman M R, Dickinson B L, Brugnara C, et al. The antifungal antibiotic, clotrimazole, inhibits chloride secretion by human intestinal T84 cells via blockade of distinct basolateral $K^+$ conductances. Demonstration of efficacy in intact rabbit colon and in an in vivo mouse model of cholera. *J Clin Invest.* 1997; 100(12):3111-20). For measurement of apical $Cl^-$ conductance, a basolateral to apical $Cl^-$ gradient is applied. The basolateral solution contained (in mM): 120 NaCl, 1 $MgCl_2$, 1 $CaCl_2$, 10 D-glucose, 5 HEPES and 25 $NaHCO_3$ (pH 7.4). In the apical solution 120 mM NaCl is replaced by 5 mM NaCl and 115 mM Na-gluconate, and the basolateral membrane is permeabilized with 250 µg/ml amphotericin B (Pongkorpsakol P, Pathomthongtaweechai N, Srimanote P, Soodvilai S, Chatsudthipong V, and Muanprasat C. Inhibition of cAMP-activated intestinal chloride secretion by diclofenac: cellular mechanism and potential application in cholera. *PLoS Negl Trop Dis.* 2014; 8(9):e3119). Short-circuit current is measured using an EVC4000 multichannel voltage clamp (World Precision Instruments, Sarasota, FL). For intestinal short-circuit current measurement, CD1 mice are anesthetized with isoflurane. The ileum is removed, washed with ice-cold Krebs buffer, opened along the mesenteric border, and full-thickness layer is mounted in a micro-Ussing chamber (area 0.7 cm2, World Precision Instruments, Sarasota, FL). Hemichambers are filled with oxygenated Krebs-bicarbonate solution.

Intracellular Calcium and cAMP Measurements

T84 cells are plated in 96-well black-walled microplates. Confluent cells are loaded with Fluo-4 NW (Invitrogen, Carlsbad, CA) at 72 h after plating. In some studies cells are pretreated for 30 min with afatinib. Fluo-4 fluorescence is measured with a Tecan Infinite M1000 plate reader (Tecan Groups Ltd, Mannedorf, Switzerland) at excitation/emission wavelengths of 495/516 nm. For cAMP assay, T84 cells are grown in 24-well plates, treated for 30 min with afatinib and/or forskolin, lysed by repeating freeze/thaw, centrifuged to remove cell debris, and the supernatant is assayed for cAMP using the Parameter cAMP immunoassay kit according to the manufacturer's instructions (R&D Systems, Minneapolis, NM).

Statistics

Data are presented as mean±S.E.M. Statistical analysis is performed using Prism 5 GraphPad Software package (San Diego, CA). Statistical comparisons are made using the Student's test or ANOVA. A value of $p<0.05$ is taken as statistically significantly.

ErbB Tyrosine Kinase Inhibitors Amplify Carbachol-Induced Current in Intestinal Cells The effect of ErbB TKIs lapatinib, gefitinib, and afatinib on $Cl^-$ secretory responses in T84 human colonic epithelial cells is tested. Short-circuit current is measured in T84 cell monolayers with identical solutions bathing the apical and basolateral surfaces. FIG. 1A shows that administration of ErbB TKIs alone do not increase short-circuit current, suggesting that they do not directly activate apical membrane $Cl^-$ channels such as CFTR or CaCCs, or other transporters involved in generating a secretory current, such as basolateral $K^+$ channels. However, addition of the ErbB TKIs prior to the muscarinic agonist carbachol significantly amplifies the subsequent $Cl^-$ secretory response by 2-3 fold. ErbB TKIs also amplify $Cl^-$ secretion induced by the purinergic agonist ATP and the $Ca^{2+}$ ATPase inhibitor thapsigargin, indicating that the TKI effect is not specific for cholinergic agonists.

FIG. 1B shows that, as in T84 cells, afatinib does not by itself increase short-circuit current in mouse ileum, but amplifies the current response to carbachol.

To test whether the effect of afatinib involves EGF signaling, short-circuit current is measured in cells pretreated with EGF alone, afatinib alone, and EGF together with afatinib (FIG. 1C). Administration of EGF greatly reduces $Cl^-$ secretion in response to carbachol. Afatinib overcomes the EGF-mediated suppression of carbachol-induced current, with similar current responses seen for cells pretreated with afatinib alone vs. EGF+afatinib. The blocking of the EGF suppression of carbachol-induced current by afatinib suggests that its amplification of the $Cl^-$ secretory response occurs via inhibition of ErbB receptor activation.

The kinetics and concentration-dependence of the afatinib-induced amplification of the carbachol response in T84 cells. FIG. 2A shows the amplifying effect of afatinib on carbachol-induced short-circuit current increased with time between afatinib and carbachol additions, with half maximal effect at 10-15 min and maximal effect seen by ~25 min. When added 25 min prior to carbachol, the afatinib effect is concentration-dependent, with EC50~5 (FIG. 2B).

Figure 3:
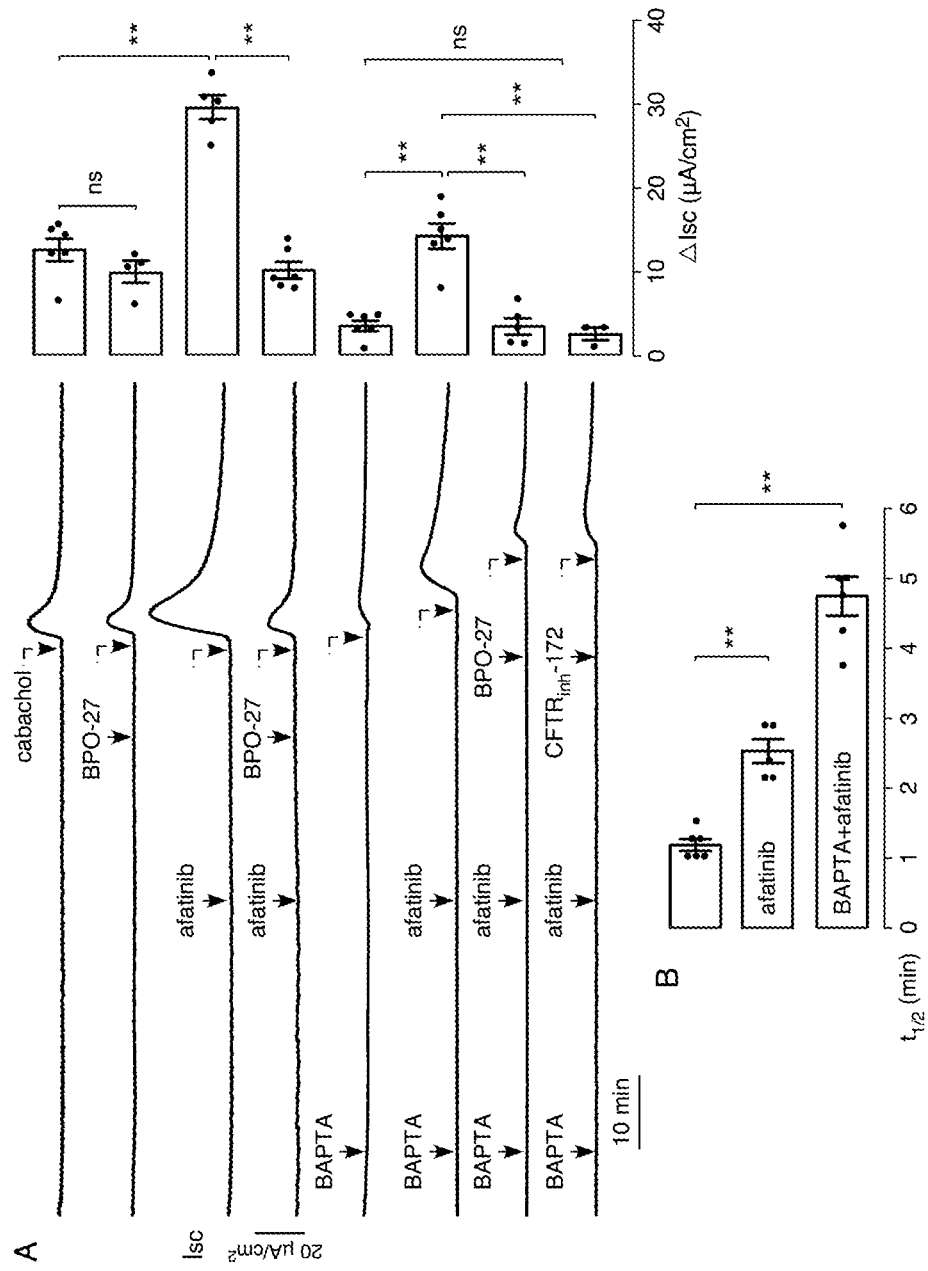
FIG. 3 shows that the afatinib-induced augmentation in carbachol current is CFTR-dependent. (A) (left) Short-circuit current in T84 cells showing effects of 20 μM afatinib, 100 μM carbachol, 10 μM BPO-27 and 10 μM CFTR$_{inh}$-172, with or without 30 μM BAPTA-AM, as indicated. (right) Summary of peak carbachol-induced current (mean±S.E.M.) (B) Half-time ($t_{1/2}$) of the decreasing phase of the carbachol response curve (mean±S.E.M.). **p<0.01.

Afatinib-Mediated Amplification of Carbachol-Induced $Cl^-$ Secretion is CFTR-Dependent Because carbachol induces $Cl^-$ secretion through activation of intracellular $Ca^{2+}$ signaling and activation of apical membrane CaCC, whether the afatinib-induced amplification of the carbachol response involves $Ca^{2+}$ elevation and CaCC activation is investigated. FIG. 3A (left) shows that the CFTR-selective inhibitor BPO-27 has little effect on the carbachol-induced current in T84 cells. However, BPO-27 blocks the afatinib augmentation of the carbachol-induced current. Treatment with BAPTA-AM to block elevation of intracellular $Ca^{2+}$ largely prevents the carbachol response. However, in the BAPTA-treated cells afatinib produces a substantial residual carbachol response, which is blocked by the two chemically unrelated CFTR inhibitors BPO-27 and $CFTR_{inh}$-172. The carbachol response curves are broader (slower return to baseline) in the presence vs. the absence of afatinib.

FIG. 3A (right) shows that the carbachol response as the maximum increase in short-circuit current (ΔIsc). The data suggest that afatinib augmentation of the carbachol-induced Cl$^-$ secretion is CFTR-dependent and does not require Ca$^{2+}$ signaling. The amplified current is blocked by CFTR inhibitors, not prevented by BAPTA treatment, and has a different character than the Ca$^{2+}$-dependent carbachol response in terms of its curve shape as quantified by $t_{1/2}$ analysis (FIG. 3B).

Afatinib does not Affect Calcium or cAMP Signaling

Figure 4:
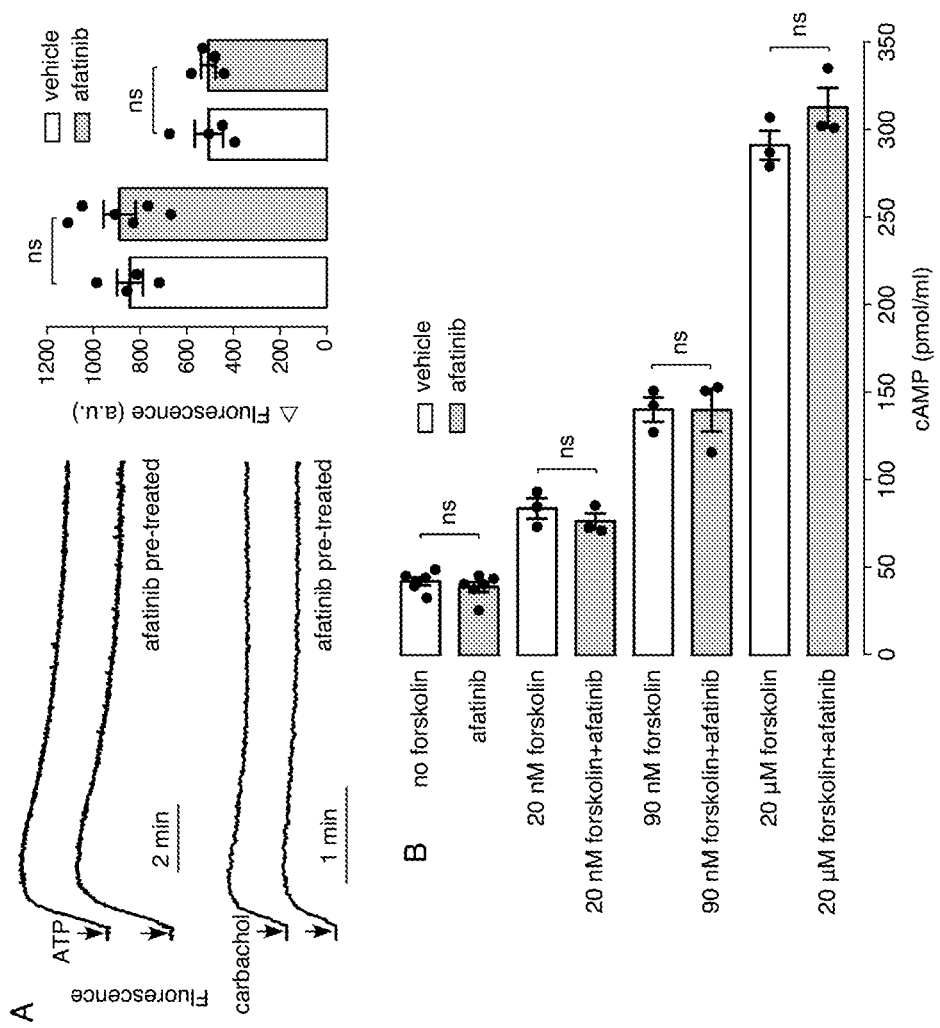
FIG. 4 shows that afatinib does not affect calcium or cAMP signaling. (A) (left) Cytoplasmic Ca$^{2+}$ concentration measured by Fluo-4 fluorescence. Afatinib (20 μM) is added 20 min prior to addition of 100 μM ATP or 100 μM carbachol. (right) Peak increase in Fluo-4 fluorescence after ATP or carbachol (mean±S.E.M.). (B) cAMP in T84 cells measured 30 min after incubation with afatinib (20 μM) or forskolin (20 nM, 90 nM, 20 with or without afatinib (20 μM) (mean±S.E.M.). ns, not significant.

The residual afatinib-amplified carbachol current in BAPTA-treated cells and its suppression by CFTR inhibitors suggests that the afatinib effect is not mediated by intracellular Ca$^{2+}$ signaling but perhaps could involve cAMP signaling. Consistent with this, afatinib does not by itself increase cytoplasmic Ca$^{2+}$ concentration, nor does it have significant effect on the transient elevations in Ca$^{2+}$ concentration following ATP or carbachol, as shown in FIG. 4A. Also, afatinib does not itself increase total cellular cAMP, nor does it affect the increase in cAMP following forskolin, as shown in FIG. 4B.

Figure 5:
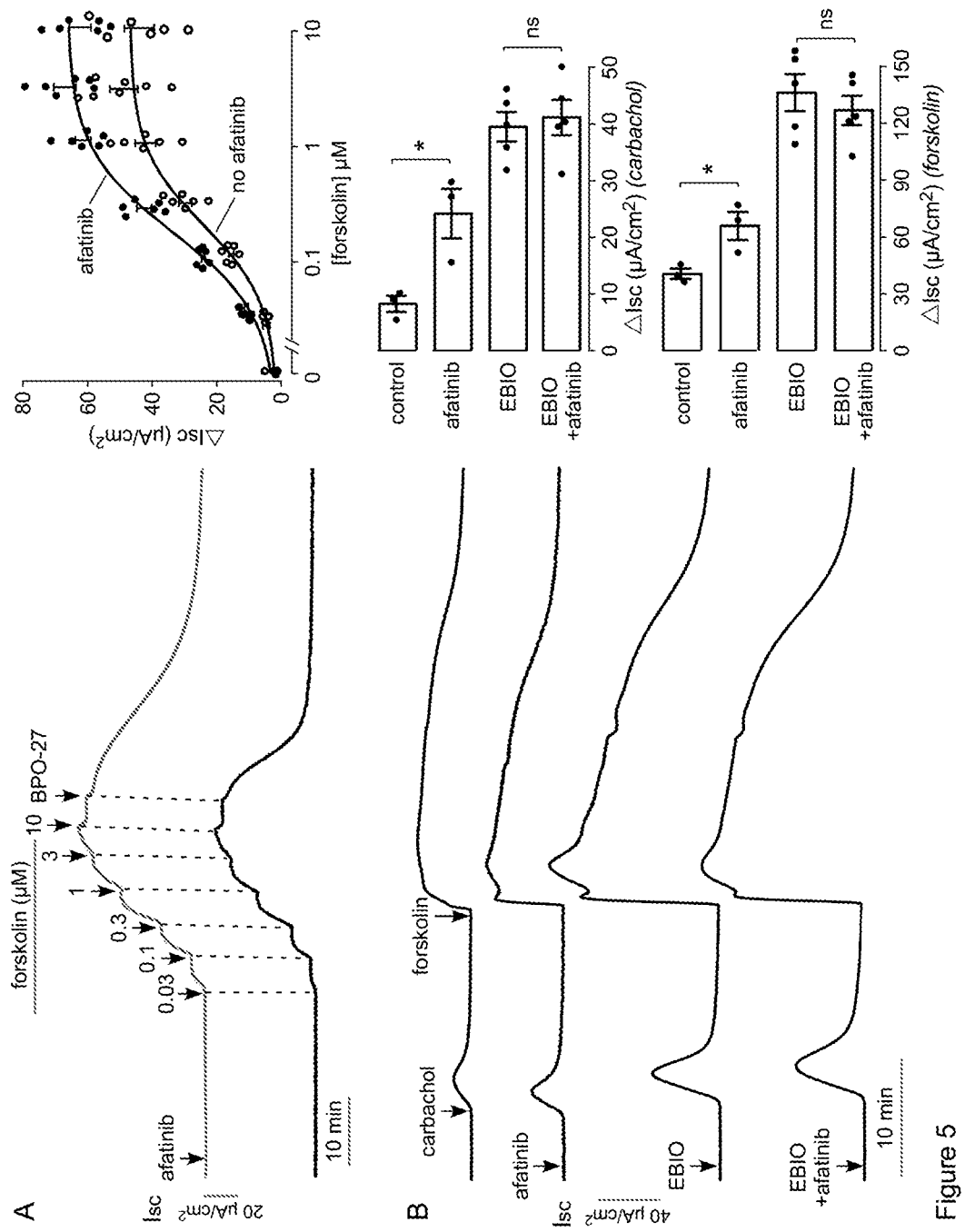
FIG. 5 shows that afatinib amplifies forskolin-induced current in T84 cells. (A) (left) Short-circuit current in T84 cells in response to 20 μM afatinib (or vehicle control) followed by indicated concentrations of forskolin, then 10 μM BPO-27. (right) Forskolin concentration-dependence of short-circuit current (mean±S.E.M.). (B) (left) Short-circuit current in T84 cells in response to additions of EBIO (500 μM) and/or afatinib (20 μM) added 25 min prior to 100 μM carbachol followed by 10 μM forksolin. (right) Summary of peak carbachol- and forskolin-induced currents. p<0.05, **p<0.01.

Afatinib Amplifies Carbachol-Induced Activation of Basolateral K+ Channels and Apical CFTR Cl$^-$ Channels Though afatinib does not affect cAMP levels, the possibility is investigated that afatinib might influence forskolin (cAMP) induced short-circuit current. Afatinib amplifies the forskolin-induced current response as shown in FIG. 5A, albeit to a lesser extent than is seen with carbachol. This result, together with the lack of effect of afatinib on intracellular Ca$^{2+}$ and cAMP, and the finding that afatinib itself does not induce a current response, suggests that the afatinib amplification of the Cl$^-$ secretory response may in part involve activation of basolateral membrane K$^+$ channel(s). The afatinib response is mimicked by EBIO, a K$^+$ channel agonist that increases the conductance of both the epithelial Ca$^{2+}$- and cAMP-activated K$^+$ channels. FIG. 5B shows that EBIO pretreatment amplifies the carbachol and forskolin current responses. Pretreatment with EBIO and afatinib together showed a similar effect to pretreatment with EBIO alone.

Figure 6:
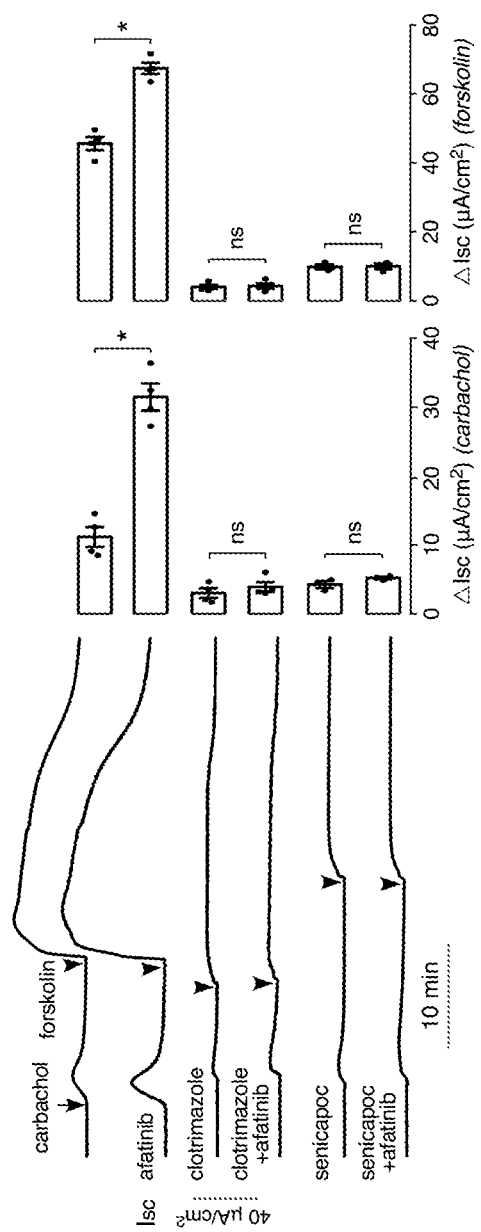
FIG. 6 shows that K$^+$ channel inhibitors block the afatinib-induced augmentation in carbachol current. (left) Short-circuit current in T84 cells treated with 20 μM afatinib, 30 μM clotrimazole and/or 10 μM senicapoc, as indicated, 30 min prior to addition of 100 μM carbachol followed by 10 μM forksolin (right) Summary of peak carbachol- and foskolin-induced peak current (mean±S.E.M. *p<0.05).
Figure 11:
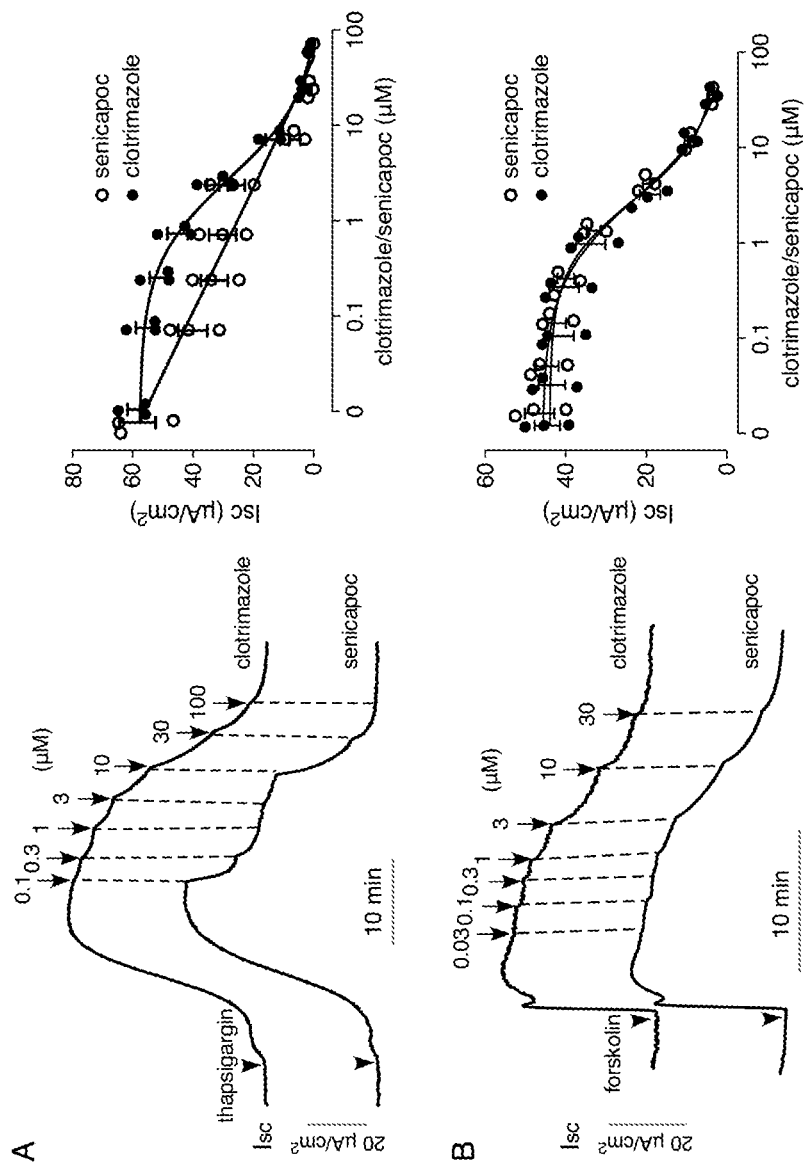
FIG. 11 shows inhibition of Ca$^{2+}$- and cAMP-activated K$^+$ channels in T84 cells by clotrimazole and senicapoc. A. (left) Short-circuit current in response to 2 μM thapsigargin (following 25 min pretreatment with 20 μM afatinib), followed by indicated concentrations of clotrimazole or senicapoc. (right) Inhibition concentration-dependence (mean±S.E.M.). (B) (left) Short-circuit current in response to 10 μM forskolin followed by clotrimazole or senicapoc. (right) Inhibition concentration-dependence (mean±S.E.M.).
Figure 12:
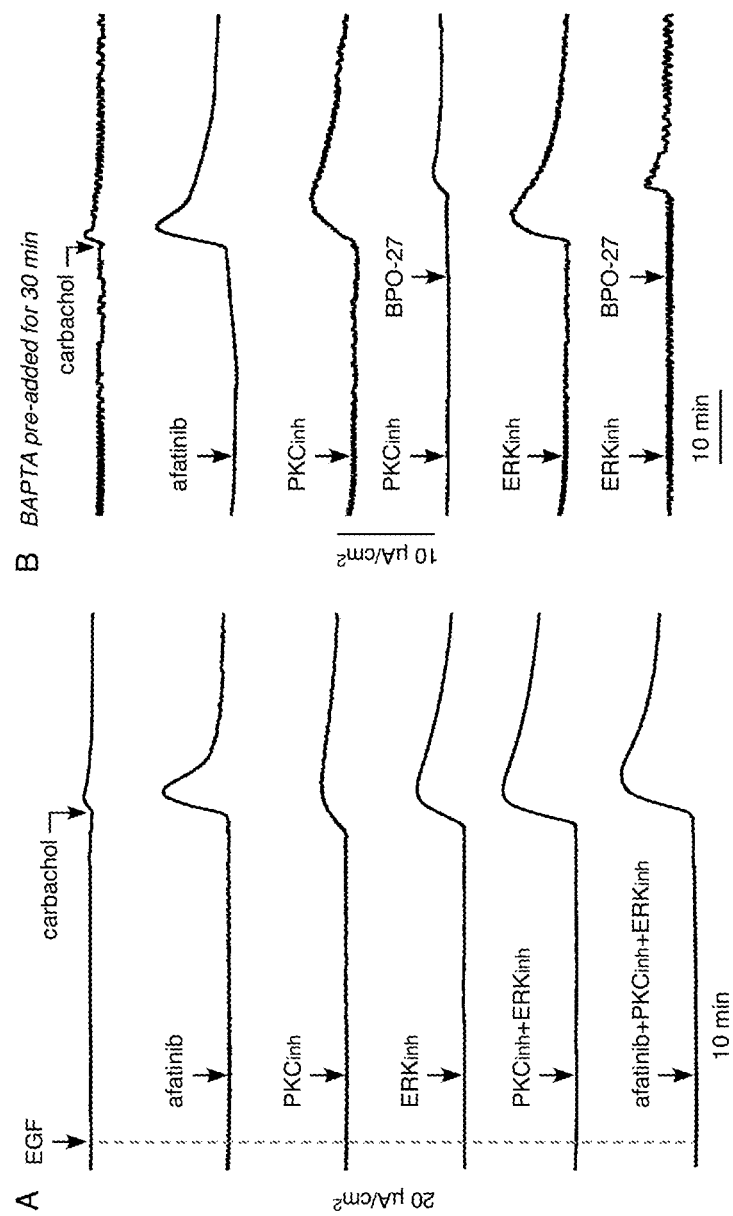
FIG. 12 shows the effect of ERK and PKC inhibitors on short-circuit current in T84 cells after treatments with EGF or BAPTA-AM. (A) Responses shown to 100 ng/ml EGF followed by 20 μM afatinib, 10 μM PKC inhibitor (Ro 31-8220), 10 μM ERK inhibitor (GDC-0994), alone and together, added 25 min prior to 100 μM carbachol. (B) Following 30 min incubation with 30 μM BAPTA-AM, short-circuit current showing following 20 μM afatinib, 10 μM PKC inhibitor, 10 μM ERK inhibitor, 10 μM BPO-27, followed by 100 μM carbachol, as indicated. Representative of 2 sets of experiments.
Figure 13:
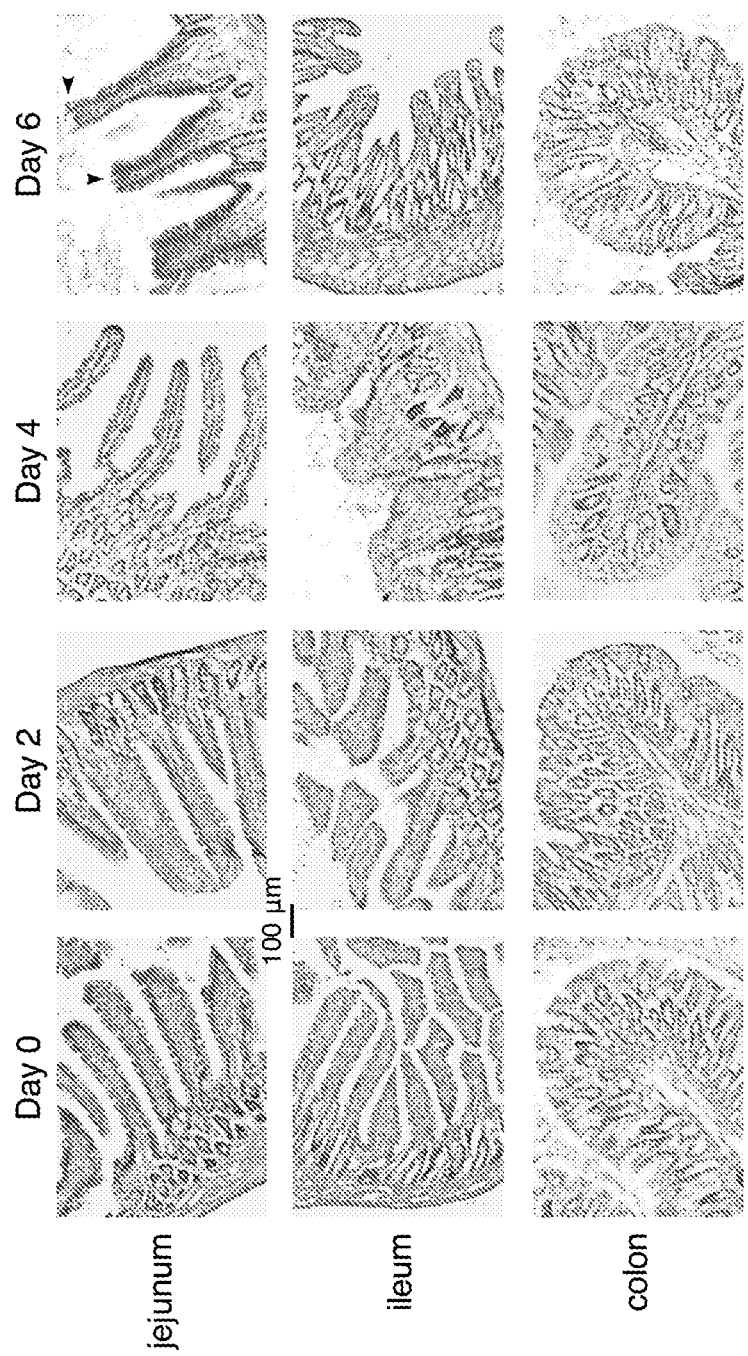
FIG. 13 shows intestinal histology of afatinib-treated rats. Sprague-Dawley rats are treated orally with afatinib (60 mg/kg) for 6 days. H&E staining showing minor injury up to day 4 with villus blunting in ileum. By day 6 scattered epithelial disruption is seen in jejunum (black arrowheads) and villus atrophy in ileum.
Figure 14:
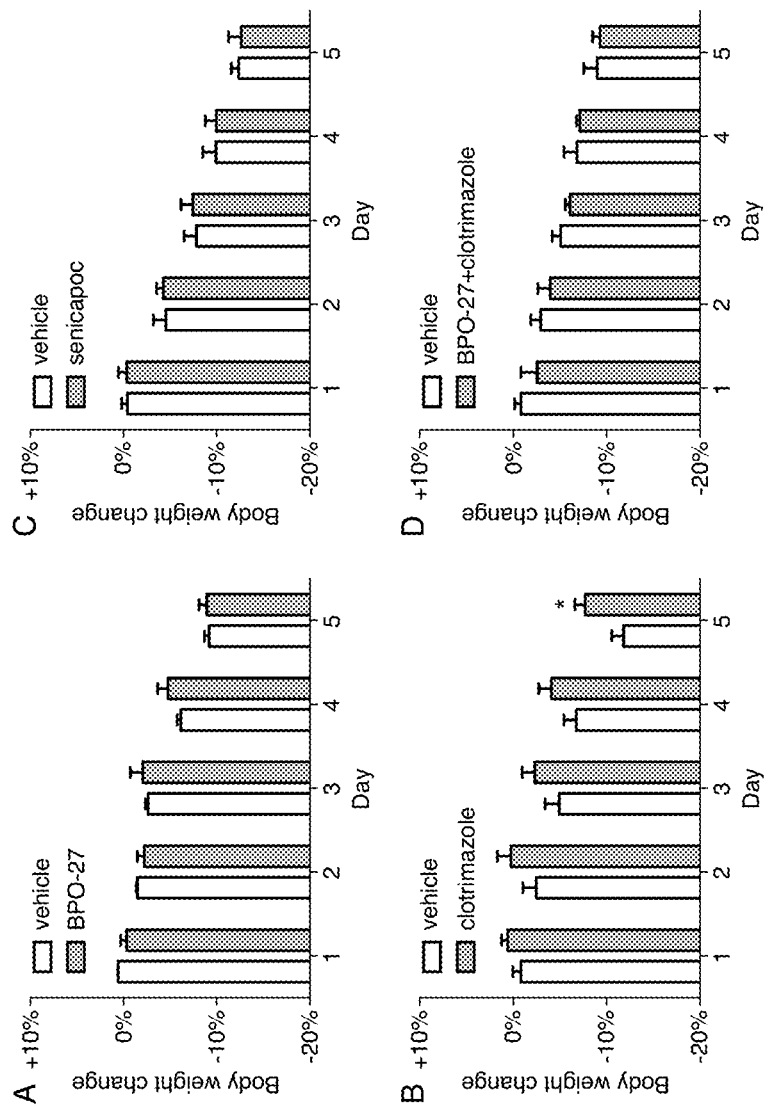
FIG. 14 shows the percentage change in rat body weight in afatinib-induced diarrhea corresponding to data in FIG. 9B-E (mean±S.E.M., *P<0.05).

The FDA-approved antifungal drug clotrimazole is a well-characterized inhibitor of the intermediate conductance Ca$^{2+}$-activated K$^+$ channel (Kca3.1) and the epithelial cAMP-activated K$^+$ channel, and the chemically related investigational drug senicapoc is an inhibitor of Kca3.1. In T84 cells, clotrimazole or senicapoc largely prevents the carbachol and forskolin induced current responses, both without and with afatinib pretreatment as shown in FIG. 6. The small residual current likely is due to the presence of other K$^+$ channels(s) rather than incomplete inhibition by clotrimazole or senicapoc, because higher concentrations of these compounds does not inhibit the residual current (data not shown); in patch-clamp studies clotrimazole has been reported to fully inhibit epithelial Ca$^{2+}$-activated K$^+$ channels. FIG. 11 shows low micromolar IC$_{50}$ for inhibition of Ca$^{2+}$- and cAMP-dependent basolateral K$^+$ conductances by clotrimazole and senicapoc.

Figure 7:
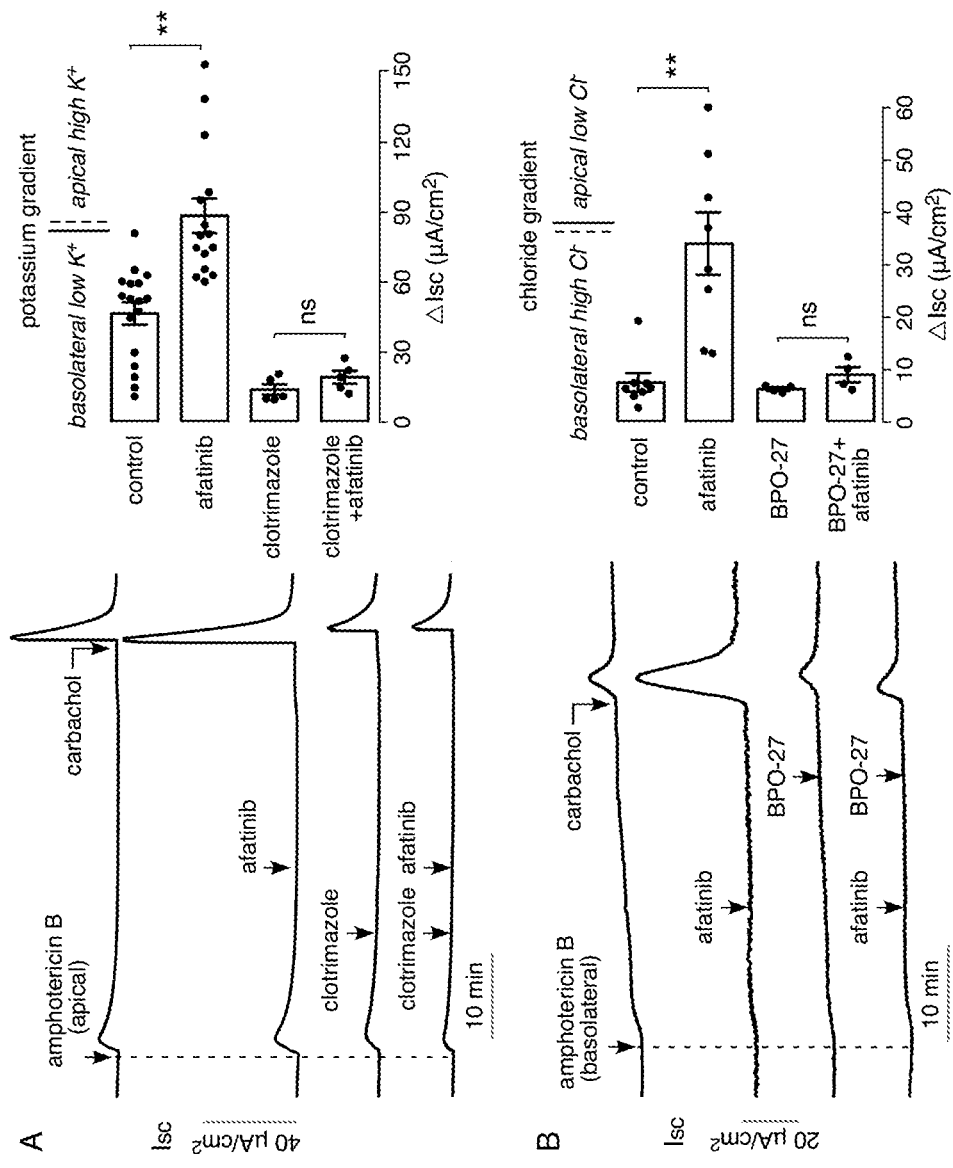
FIG. 7 shows that afatinib amplifies carbachol-induced activation of basolateral K$^+$ conductance and apical CFTR Cl$^-$ conductance. (A) (left) Short-circuit current in T84 cells following apical membrane permeabilization with 20 μM amphotericin B in the presence of an apical-to-basolateral solution K$^+$ gradient (apical [K$^+$] 142 mM, basolateral [K$^+$] 5 mM). Afatinib (20 μM) and carbachol (100 μM) added as indicated. (right) Summary of peak carbachol-induced current (mean±S.E.M.). (B) (left) Short-circuit current in T84 cells following basolateral membrane permeabilization with 250 μg/ml amphotericin B in the presence of a basolateral-to-apical solution Cl$^-$ gradient (basolateral [Cl$^-$] 120 mM, apical [Cl$^-$] 5 mM). Afatinib (20 BPO-27 (10 μM) and carbachol (100 μM) added as indicated. (right) Summary of peak carbachol-induced current (mean±S.E.M.). **p<0.01.
Figure 8:
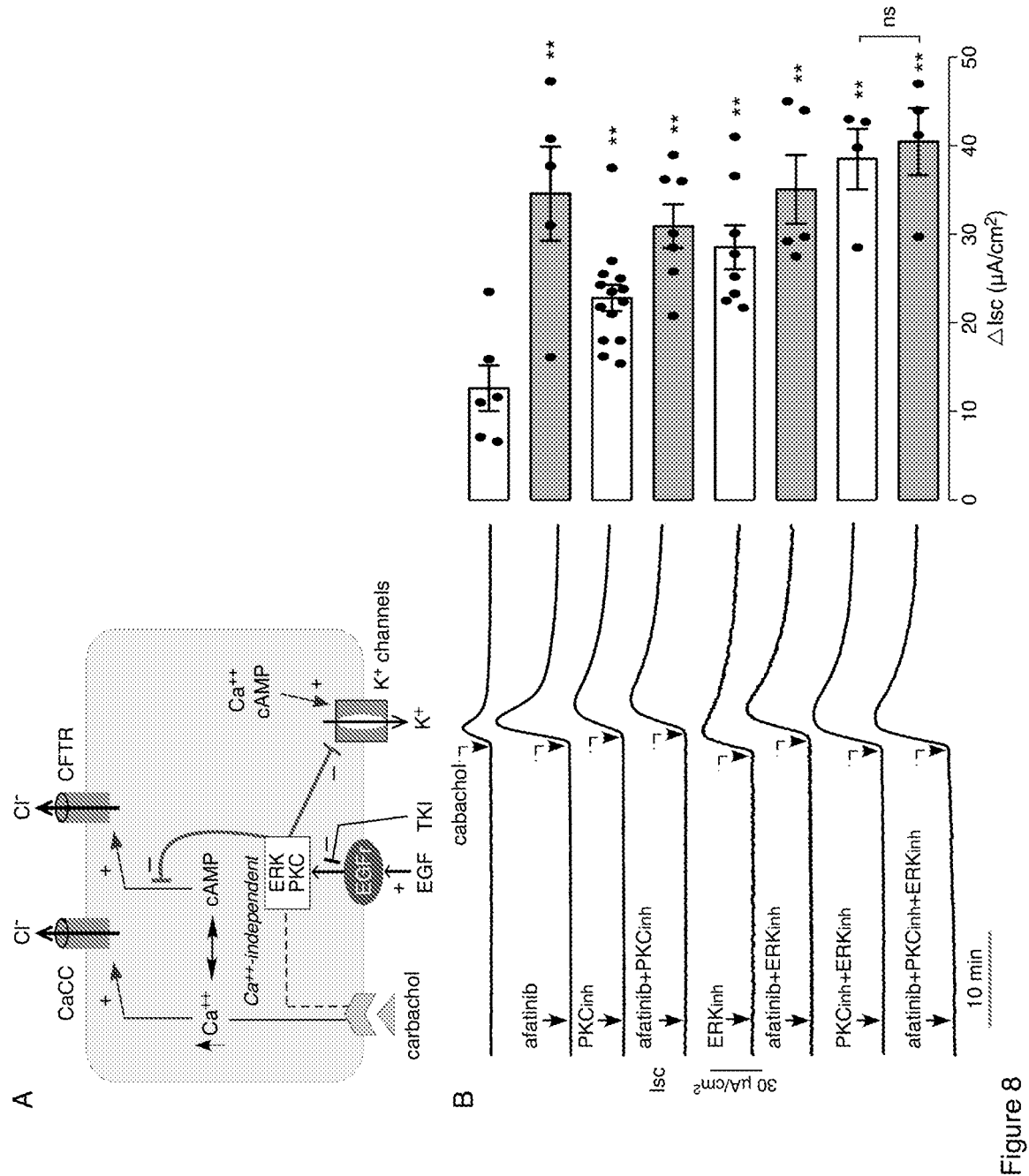
FIG. 8 shows Involvement of ERK and PKC signaling in afatinib amplification of secretion. (A) Schematic of proposed mechanism of TKI action. EGF binding to its receptor (EGFr) inhibits activation of basolateral K$^+$ channels and apical Cl$^-$ channels via PKC and ERK signaling. TKI abolishes this inhibition. (B) (left) Short-circuit current in T84 cells showing responses to afatinib (20 PKC inhibitor (Ro 31-8220, 10 ERK inhibitor (GDC-0994, 10 alone or together, added 25 min prior to 100 μM carbachol. (right) Summary of peak carbachol-induced current (mean±S.E.M., *p<0.05, **p<0.01).

To measure basolateral membrane K$^+$ conductance directly, short-circuit current is measured in T84 cells following permeabilization of the apical membrane with amphotericin B in Cl$^-$ and Na$^+$ free solutions and an apical-to-basolateral K$^+$ gradient (FIG. 7A). Afatinib pretreatment produced a ~2-fold increase in the carbachol response, which is largely blocked by clotrimazole. Afatinib therefore amplifies the opening of basolateral membrane K$^+$ channel(s) in response to carbachol in T84 cells.

Figure 2:
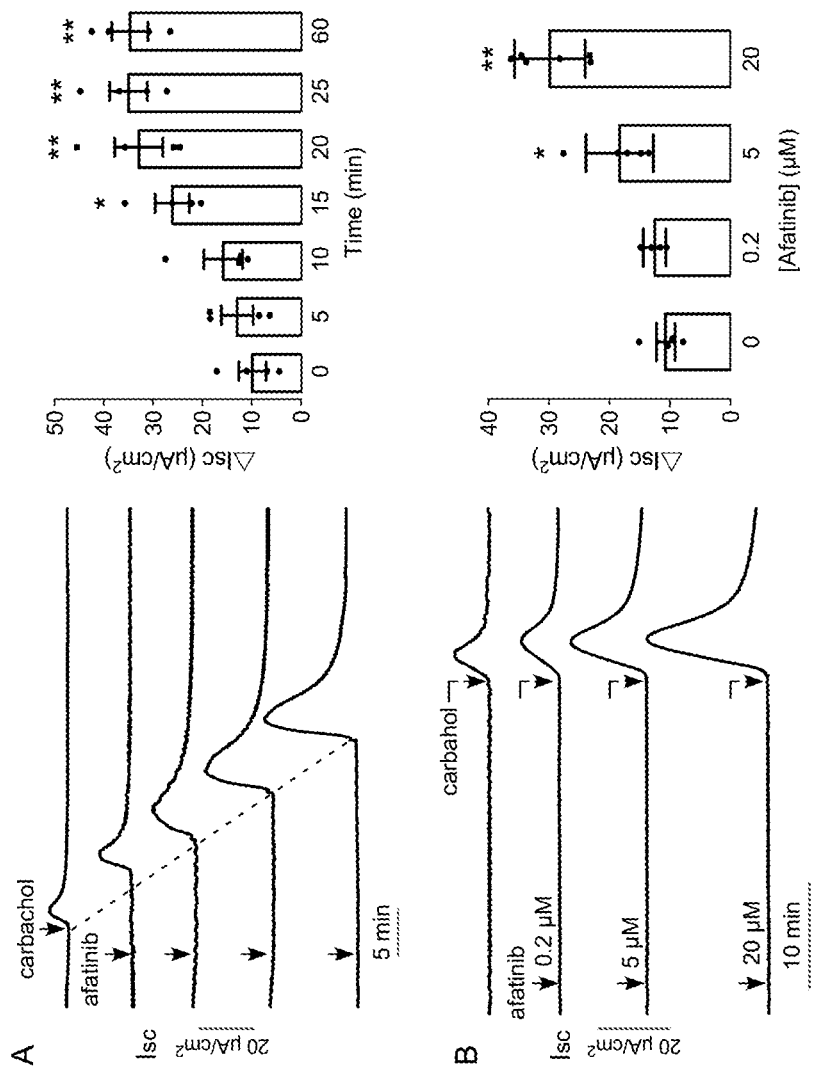
FIG. 2 shows the kinetics and concentration-dependence of afatinib amplification of carbachol response. (A) (left) Time course of afatinib effect on carbachol-induced short-circuit current in T84 cells. Cells treated with 20 μM afatinib for different times prior to 100 μM carbachol. (right) Summary of peak carbachol-induced current (mean±S.E.M.). (B) (left) Concentration-dependence of afatinib effect. (right) Summary of peak current (mean±S.E.M.). *$p<0.05$, **$p<0.01$.

In addition to afatinib action on amplifying basolateral K$^+$ channel activation, the data in FIG. 2 indicates that afatinib also amplifies apical CFTR Cl$^-$ channel activation. Short-circuit current is measured following permeabilization of the basolateral membrane and with a basolateral-to-apical Cl$^-$ gradient (FIG. 7B). Afatinib pretreatment produces a >4-fold increase in the carbachol response, which is blocked by BPO-27. The amplified carbachol response with afatinib therefore also involves increased activation of apical membrane CFTR Cl— channels.

Afatinib-Induced Diarrhea in Rats is Reduced by Inhibitors of K$^+$ Channels and CFTR Cl$^-$ Channels Rat Model of Afatinib Diarrhea Female Sprague-Dawley rats (age 8-10 weeks) received oral afatinib (60 mg/kg oral) daily for 6 days. BPO-27 (10 mg/kg, ip), clotrimazole (100 mg/kg, oral) or senicapoc (30 mg/kg, oral), or (R)—BPO-27+clotrimazole, is administered twice daily to afatinib-treated rats. (R)—BPO-27 and senicapoc are dissolved in saline containing 5% DMSO and 10% Kolliphor H S. Clotrimazole is dispersed in peanut oil and sonicated for 30 min. Rats are placed individually in metabolic cages and given access to water and food. Stool samples are collected for 5 hours. To measure stool water content, the stool samples are dried at 70° C. for 24 hours and water content is calculated as (wet weight–dry weight)/wet weight.

Figure 9:
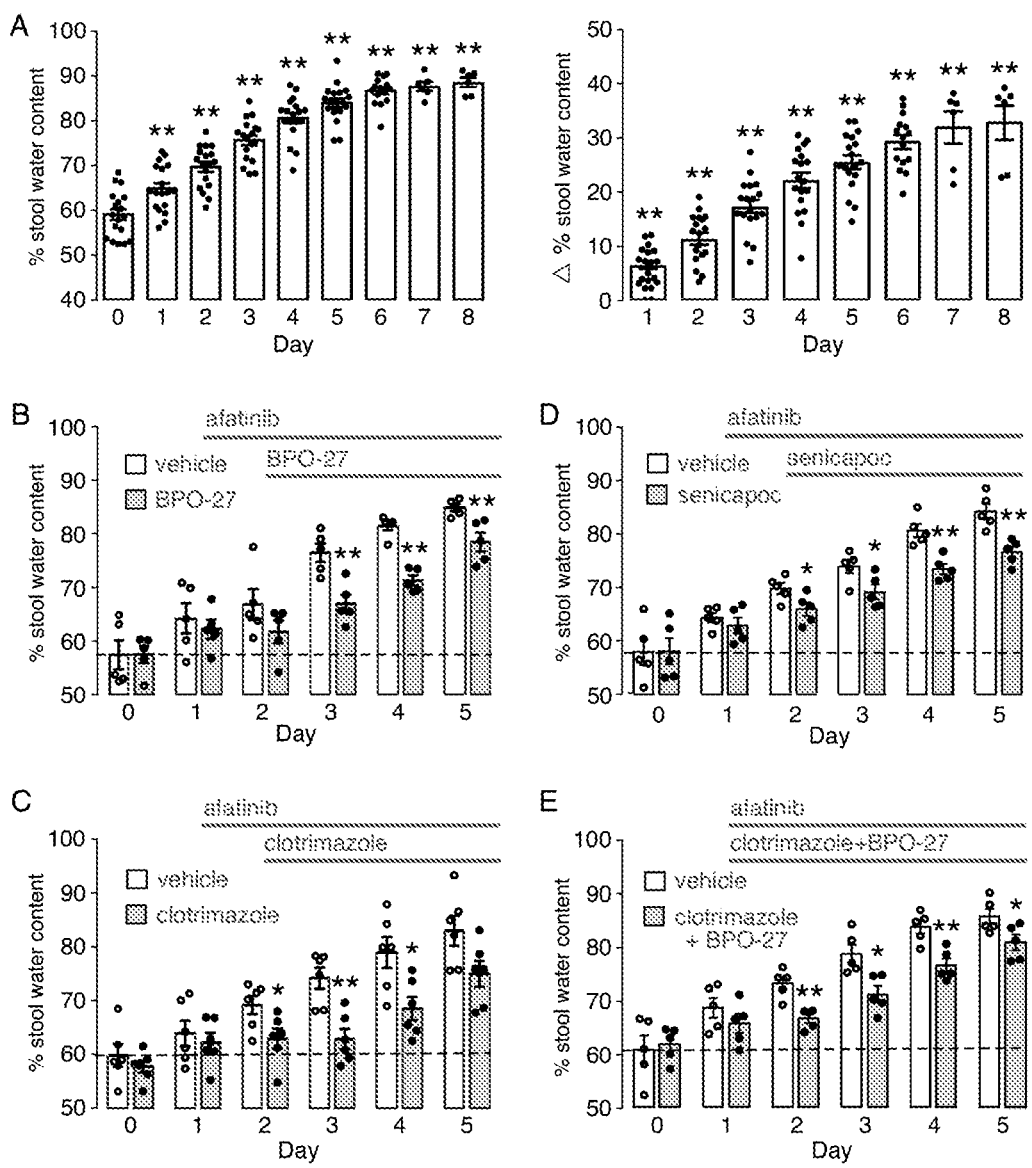
FIG. 9 shows that inhibitors of K$^+$ channels and CFTR Cl$^-$ channels reduce afatinib-induced diarrhea in rats. (A) Afatinib diarrhea model in Sprague-Dawley rats administered afatinib orally (60 mg/kg, daily). (left) Stool water content (percentage water) as measured daily. (right) Increase in stool water content in individual rats (stool water at indicated data minus stool water on day 0 in same rats). (B) Rats are administered afatinib starting on day 1, and treated starting on day 2 with BPO-27 (10 mg/kg, twice daily, ip) or vehicle. (C) Similar protocol as in B, except for treatment with clotrimazole (100 mg/kg, oral in two divided doses) or vehicle. (D) Similar protocol as in B, except for treatment with senicapoc (30 mg/kg, oral, twice daily) or vehicle. (E) Similar protocol except for treatment starting on day 1 with clotrimazole and BPO-27 (same doses as in B and C) or vehicle All data reported as mean±S.E.M. *p<0.05, **p<0.01, comparing with day 0 in A. and with vs. without drug treatment in B.-E.
Figure 10:
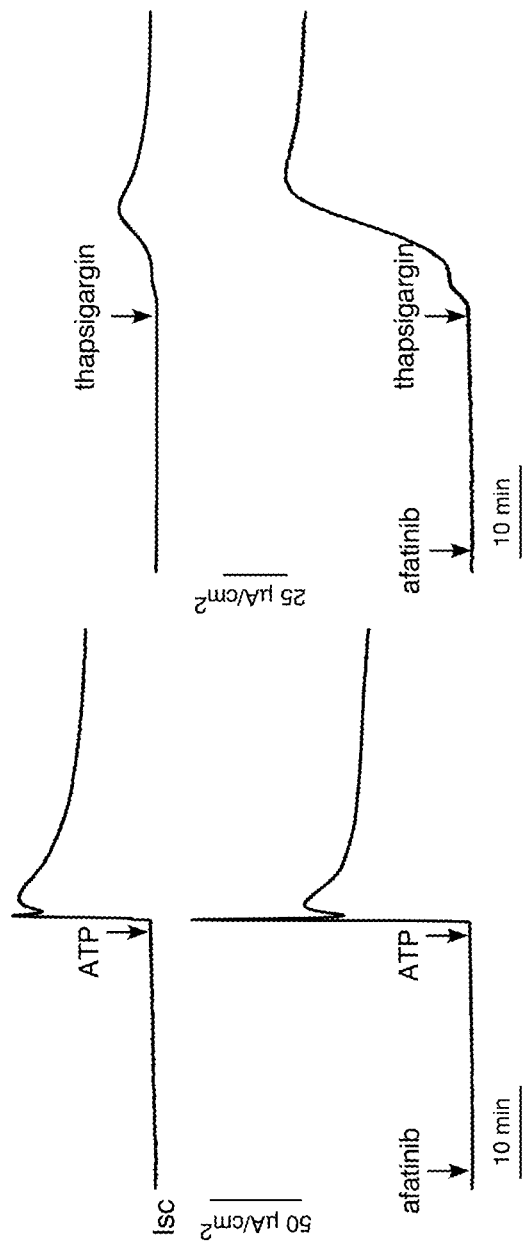
FIG. 10 shows that afatinib amplifies ATP- and thapsigargin-induced short-circuit current in T84 cells. Responses shown to 20 μM afatinib added 25 min prior to 100 μM ATP (left) or 2 μM thapsigargin (right). Representative of 3 sets of experiments.

Following initial dose-finding studies in mice and rats with several TKIs, using stool water content (from wet and dry weight measurement) as endpoint, a robust, short-term experimental animal model of afatinib diarrhea is established involving daily oral administration of 60 mg/kg afatinib in rats. By days 4-5, stool water content, determined by stool wet-to-dry weight ratio, increased to >80% over the baseline of ~60% (FIG. 9A). Examination of intestinal histology showed relatively minor pathology up to day 4, but greater epithelial disruption after that. A 5-day afatinib model is then used to test the potential antidiarrheal effect of the K$^+$ channel blockers clotrimazole and senicapoc, and the CFTR inhibitor BPO-27.

Treatment of rats with BPO-27 at 10 mg/kg intraperitoneally twice daily, starting 1 day after the first afatinib dose, produced a significant reduction in the increased stool water content with afatinib (FIG. 9B). The BPO dosing is selected from prior pharmacokinetics data in mice (Cil O, Phuan P W, Gillespie A M, Lee S, Tradtrantip L, Yin J, et al. Benzopyrimido-pyrrolo-oxazine-dione CFTR inhibitor (R)—BPO-27 for antisecretory therapy of diarrheas caused by bacterial enterotoxins. *FASEB J.* 2017; 31(2):751-60) and preliminary studies in rats to produce predicted therapeutic concentrations in serum. The increase in stool water content is inhibited by ~50% on days 3 and 4. The reduced inhibitor effect by day 5 may be related to afatinib-induced epithelial injury in this model and an increase in the non-secretory component of diarrhea.

Oral treatment of rats with clotrimazole at 100 mg/kg (oral in two divided doses), a dose and administration regimen chosen from published data (Takei S, Iseda T, and Yokoyama M. Inhibitory effect of clotrimazole on angiogenesis associated with bladder epithelium proliferation in rats. *Int J Urol.* 2003; 10(2):78-85; Khalid M H, Tokunaga Y, Caputy A J, and Walters E. Inhibition of tumor growth and prolonged survival of rats with intracranial gliomas following administration of clotrimazole. *J Neurosurg.* 2005; 103 (1):79-86; Rufo P A, Merlin D, Riegler M, Ferguson-Maltzman M H, Dickinson B L, Brugnara C, et al. The antifungal antibiotic, clotrimazole, inhibits chloride secretion by human intestinal T84 cells via blockade of distinct basolateral K$^+$ conductances. Demonstration of efficacy in intact rabbit colon and in an in vivo mouse model of cholera. *J Clin Invest.* 1997; 100(12):3111-20)), also significantly reduced the increase in stool water content in afatinib-treated rats, with ~75% inhibition on days 3 and 4 (FIG. 9D). Significant, though lesser reduction in the increase in stool water content is found for senicapoc at 30 mg/kg twice daily, a dose chosen from published data (Staal R G W, Khayrullina T, Zhang H, Davis S, Fallon S M, Cajina M, et al. Inhibition of the potassium channel KCa3.1 by senicapoc reverses tactile allodynia in rats with peripheral nerve injury. *Eur J Pharmacol.* 2017; 795:1-7; Paka L, Smith D E, Jung D, McCormack S, Zhou P, Duan B, et al. Anti-steatotic and anti-fibrotic effects of the KCa3.1 channel inhibitor, Senicapoc, in non-alcoholic liver disease. *World J Gastroenterol.* 2017; 23(23):4181-90).

Without being bound by theory, the data here suggest that ErbB TKIs induce Cl$^-$ secretion by preventing EGF-mediated ERK activity, which normally acts to limit both basolateral K$^+$ and apical Cl$^-$ channel activity. Loss of ERK-mediated inhibition therefore results in amplified channel activity and excessive fluid secretion. The data here support a prosecretory mechanism for ErbB TKI diarrhea involving amplified activity of K$^+$ channels at the basolateral membrane of intestinal epithelial cells and CFTR Cl$^-$ channels at the apical membrane.

The present disclosure is also directed to the following aspects:

Aspect 1. A method of treating a subject with tyrosine kinase inhibitor-induced diarrhea, comprising administering to the subject an amount of a potassium channel inhibitor, or an amount of a CFTR chloride channel inhibitor, or a combination of a potassium channel inhibitor and CFTR chloride channel inhibitors, effective to treat the tyrosine kinase inhibitor-induced diarrhea.

Aspect 2. The method of aspect 1, wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

Aspect 3. The method of aspect 2, wherein the tyrosine kinase inhibitor is afatinib, canertinib, cetuximab, erlotinib, gefitinib, or lapatinib; or a pharmaceutically acceptable salt thereof, or a combination thereof.

Aspect 4. The method of aspect 3, wherein the tyrosine kinase inhibitor is afatinib, or a pharmaceutically acceptable salt thereof.

Aspect 5. The method of any one of the preceding aspects, wherein the potassium channel is a Ca$^{2+}$-activated potassium channel.

Aspect 6. The method of any one of the preceding aspects, wherein the potassium channel inhibitor is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof.

Aspect 7. The method of any one of the preceding aspects, wherein the CFTR chloride channel inhibitor is (R)—BPO-27, CFTR$_{inh}$-172, GlyH-101, glibenclamide, diphenylamine-2-carboxylate, 5-nitro-2-(3-phenylpropylamino) benzoate, or niflumic acid, or a combination thereof.

Aspect 8. The method of any one of the preceding aspects, wherein the CFTR chloride channel inhibitor is (R)—BPO-27.

Aspect 9. A method of reducing intestinal fluid secretion resulting from tyrosine kinase inhibitor-induced activation of potassium channels or tyrosine kinase inhibitor-induced activation of CFTR chloride channels in the intestinal epithelium in a subject in need thereof, comprising administering to the subject an amount of a potassium channel inhibitor, or an amount of a CFTR chloride channel inhibitor, or an amount of combination of a potassium channel inhibitor and CFTR channel inhibitor, effective to reduce said intestinal fluid secretion.

Aspect 10. The method of aspect 9, wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

Aspect 11. The method of aspect 10, wherein the tyrosine kinase inhibitor is afatinib, canertinib, cetuximab, erlotinib, gefitinib, or lapatinib; or a pharmaceutically acceptable salt thereof, or a combination thereof.

Aspect 12. The method of aspect 11, wherein the tyrosine kinase inhibitor is afatinib, or a pharmaceutically acceptable salt thereof.

Aspect 13. The method of any one aspects 9-12, wherein the potassium channel inhibitor is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof.

Aspect 14. The method of any one of aspects 9-13, wherein the CFTR chloride channel inhibitor is (R)—BPO-27, CFTR$_{inh}$-172, GlyH-101, glibenclamide, diphenylamine-2-carboxylate, 5-nitro-2-(3-phenylpropylamino) benzoate or niflumic acid, or a combination thereof.

Aspect 15. The method of aspect 14, wherein the CFTR chloride channel inhibitor is (R)—BPO-27.

Aspect 16. A method of reducing tyrosine kinase inhibitor-induced potassium channel current or tyrosine kinase inhibitor-induced CFTR chloride channel current in the intestinal epithelium of a subject in need thereof, comprising administering to the subject an amount of a potassium channel inhibitor, or an amount of a CFTR chloride channel inhibitor, or an amount of combination of a potassium channel inhibitor and CFTR channel inhibitor, effective to reduce said tyrosine kinase inhibitor-induced potassium channel current or said tyrosine kinase inhibitor-induced CFTR chloride channel current.

Aspect 17. The method of aspect 16, wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

Aspect 18. The method of aspect 17, wherein the tyrosine kinase inhibitor is afatinib, canertinib, cetuximab, erlotinib, gefitinib, or lapatinib; or a pharmaceutically acceptable salt thereof, or a combination thereof.

Aspect 19. The method of aspect 18, wherein the tyrosine kinase inhibitor is afatinib, or a pharmaceutically acceptable salt thereof.

Aspect 20. The method of any one aspects 16-19, wherein the potassium channel inhibitor is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof.

Aspect 21. The method of any one of aspects 16-20, wherein the CFTR chloride channel inhibitor is (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof.

Aspect 22. The method of aspect 21, wherein the CFTR chloride channel inhibitor is (R)—BPO-27.

Aspect 23. An improvement to a method of treating cancer in a subject consisting essentially of administering to the subject an amount of a tyrosine kinase inhibitor effective to treat the subject's cancer, the improvement comprising: administering a potassium channel inhibitor, or a CFTR chloride channel inhibitor, or a combination of a potassium channel inhibitor and CFTR chloride channel inhibitor, in an amount effective to treat tyrosine kinase inhibitor-induced diarrhea in the subject.

Aspect 24. The improvement of aspect 23, wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

Aspect 25. The improvement of aspect 24, wherein the tyrosine kinase inhibitor is afatinib, canertinib, cetuximab, erlotinib, gefitinib, or lapatinib; or a pharmaceutically acceptable salt thereof, or a combination thereof.

Aspect 26. The improvement of aspect 25, wherein the tyrosine kinase inhibitor is afatinib, or a pharmaceutically acceptable salt thereof.

Aspect 27. The improvement of any one aspects 23-26, wherein the potassium channel inhibitor is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof.

Aspect 28. The improvement of any one of aspects 23-27, wherein the CFTR chloride channel inhibitor is (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof.

Aspect 29. The improvement of aspect 28, wherein the CFTR chloride channel inhibitor is (R)—BPO-27.

Aspect 30. A method of treating diarrhea in a subject being administered a tyrosine kinase inhibitor comprising determining whether the diarrhea is tyrosine kinase inhibitor-induced diarrhea; and if said determination is that the diarrhea is tyrosine kinase inhibitor-induced diarrhea, administering to the subject an amount of a potassium channel inhibitor, or an amount of a CFTR chloride channel inhibitor, or an amount of a combination of a potassium channel inhibitor and CFTR chloride channel inhibitor, effective to treat the diarrhea.

Aspect 31. The method of aspect 30, wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

Aspect 32. The method of aspect 31, wherein the tyrosine kinase inhibitor is afatinib, canertinib, cetuximab, erlotinib, gefitinib, or lapatinib; or a pharmaceutically acceptable salt thereof, or a combination thereof.

Aspect 33. The method of aspect 32, wherein the tyrosine kinase inhibitor is afatinib, or a pharmaceutically acceptable salt thereof.

Aspect 34. The method of any one aspects 30-33, wherein the potassium channel inhibitor is clotrimazole, senicapoc, nitrendipine, 4-[[3-(trifluoromethyl)phenyl]methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof.

Aspect 35. The method of any one of aspects 30-34, wherein the CFTR chloride channel inhibitor is (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof.

Aspect 36. The method of aspect 35, wherein the CFTR chloride channel inhibitor is (R)—BPO-27.

Aspect 37. A method of treating cancer in a subject, comprising administering to the subject an amount of a tyrosine kinase inhibitor effective to treat the subject's cancer; and a potassium channel inhibitor, or a CFTR chloride channel inhibitor, or a combination of a potassium channel inhibitor and CFTR chloride channel inhibitor, in an amount effective to treat tyrosine kinase inhibitor-induced diarrhea in the subject.

Aspect 38. The method of aspect 37, wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

Aspect 39. The method of aspect 38, wherein the tyrosine kinase inhibitor is afatinib, canertinib, cetuximab, erlotinib, gefitinib, or lapatinib; or a pharmaceutically acceptable salt thereof, or a combination thereof.

Aspect 40. The method of aspect 39, wherein the tyrosine kinase inhibitor is afatinib, or a pharmaceutically acceptable salt thereof.

Aspect 41. The method of any one aspects 37-40, wherein the potassium channel inhibitor is clotrimazole, senicapoc, nitrendipine, 4-[[3-(trifluoromethyl)phenyl] methyl]-2h-1,4-benzothiazin-3(4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof.

Aspect 42. The method of any one of aspects 37-41, wherein the CFTR chloride channel inhibitor is (R)—BPO-27, $CFTR_{inh}$-172, GlyH-101, glibenclamide, diphenylamine-2-carboxylate, 5-nitro-2-(3-phenylpropylamino) benzoate or niflumic acid, or a combination thereof.

Aspect 43. The method of aspect 42, wherein the CFTR chloride channel inhibitor is (R)—BPO-27.

Aspect 44. The method of any one of aspects 37-43, wherein the cancer is adenoid cystic carcinoma, adrenal gland tumor, anal cancer, bile duct cancer, bladder cancer, bone cancer, brain tumor, breast cancer, breast cancer in men, carcinoid tumor, cervical cancer, colorectal cancer, ductal carcinoma, endometrial cancer, esophageal cancer, gastric cancer, gastrointestinal stromal tumor—GIST, HER2-positive breast cancer, kidney cancer, laryngeal cancer, leukemia, liver cancer, lobular carcinoma, lung cancer, non-small cell lung cancer (NSCLC), head and neck cancers, Hodgkin's lymphoma, non-Hodgkin's lymphoma, malignant glioma, melanoma, meningioma, multiple endocrine neoplasia type 1, multiple endocrine neoplasia type 2, multiple myeloma, nasopharyngeal cancer, neuroendocrine tumor, nevoid basal cell carcinoma syndrome, oral cancer, osteosarcoma, ovarian cancer, pancreatic cancer, pancreatic neuroendocrine tumors, parathyroid cancer, penile cancer, peritoneal cancer, pituitary gland tumor, prostate cancer, renal cell cancer, retinoblastoma, salivary gland cancer, sarcoma, skin cancer (non-melanoma), small bowel cancer, stomach cancer, testicular cancer, thyroid cancer, uterine (endometrial) cancer, or vaginal cancer.

Aspect 45. The method of aspect 44, wherein the cancer is breast cancer, HER2-positive breast cancer, non-small cell lung cancer (NSCLC), or head and neck cancer.

Aspect 46. The method of any one of aspects 37-45, wherein the tyrosine kinase inhibitor is administered simultaneously with the potassium channel inhibitor, or a CFTR chloride channel inhibitor, or a combination of a potassium channel inhibitor and CFTR chloride channel inhibitor.

Aspect 47. The method of any one of aspects 37-45, wherein the tyrosine kinase inhibitor is administered before the potassium channel inhibitor, or a CFTR chloride channel inhibitor, or a combination of a potassium channel inhibitor and CFTR chloride channel inhibitor.

Aspect 48. The method of any one of aspects 37-45, wherein the tyrosine kinase inhibitor is administered after the potassium channel inhibitor, or a CFTR chloride channel inhibitor, or a combination of a potassium channel inhibitor and CFTR chloride channel inhibitor.

Aspect 49. The method of any one of aspects 37-48, wherein the subject has a mutation in a gene encoding an ErbB family member.

Aspect 50. The method of aspect 49, wherein the ErbB gene is epidermal growth factor receptor (EGFR).

Aspect 51. The method of aspect 50, wherein the mutation is in exon 18.

Aspect 52. The method of aspect 50 or 51, wherein the mutation is in the codon encoding the amino acid at position E709, G719, or a combination thereof.

Aspect 53. The method of aspect 52, wherein the mutation encodes E709K, E709A, E709G, E709V, E709H, G719A, G719S, G719C, G719D, G719V, or a combination thereof.

Aspect 54. The method of any one of aspect 50-51, wherein the mutation comprises an exon 18 deletion.

Aspect 55. The method of aspect 54, wherein the exon 18 deletion is DelE709_T710insD.

Aspect 56. The method of any one aspects 7, 8, 14, 15, 21, 22, 28, 29, 35, 36, 42, 43, or 44-55, wherein said (R)—BPO-27 is administered as a racemic mixture with (S)—BPO-27.

What is claimed:

1. A method of:
treating a subject with tyrosine kinase inhibitor-induced diarrhea,
said method comprising administering to said subject a combination of a potassium channel inhibitor and (R)—BPO-27, wherein the potassium channel inhibitor is clotrimazole, senicapoc, nitrendipine, 4-[3-(trifluoromethyl)phenyl]methyl]-2h-1,4-benzothiazin-3 (4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof;
wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

2. The method according to claim 1, wherein the tyrosine kinase inhibitor is afatinib, canertinib, cetuximab, erlotinib, gefitinib, or lapatinib; or a pharmaceutically acceptable salt thereof, or a combination thereof.

3. The method according to claim 2, wherein the tyrosine kinase inhibitor is afatinib, or a pharmaceutically acceptable salt thereof.

4. The method according to claim 1, wherein the potassium channel is a $Ca^{2+}$-activated potassium channel.

5. The method according to claim 1 wherein said (R)—BPO-27 is administered as a racemic mixture with (S)—BPO-27.

6. A method of treating diarrhea in a subject being administered a tyrosine kinase inhibitor, said method comprising:
   (i) determining if the diarrhea is tyrosine kinase inhibitor-induced diarrhea; and
   (ii) administering to said subject a combination of a potassium channel inhibitor and (R)—BPO-27, wherein the potassium channel inhibitor is clotrimazole, senicapoc, nitrendipine, 4-[[3-(trifluoromethyl)phenyl]methyl]-2h-1,4-benzothiazin-3 (4h)-one, paxilline, penitrem A, 1-[(2-chlorophenyl)diphenylmethyl]-1h-pyrazole, 2-chloro-α,α-diphenylbenzeneacetonitrile, UCL 1684, n-trityl-3-pyridinemethanamine, or methyl 4-[4-chloro-3-(trifluoromethyl)phenyl]-6-methyl-3-oxo-4,7-dihydro-1h-2-benzofuran-5-carboxylate, or a combination thereof;
   wherein the tyrosine kinase inhibitor is afatinib, axitinib, bosutinib, canertinib, crizotinib, cabozantinib, dasatinib, EKB-569, entrectinib, erlotinib, fostamatinib, gefitinib, ibrutinib, imatinib, lapatinib, leflunomide, lenvatinib, neratinib, nilotinib, pazopanib, ruxolitinib, semaxinib, sorafenib, sunitinib, SU6656, sutent, vandetanib, or vatalanib; or a pharmaceutically acceptable salt thereof, or a combination thereof.

7. The method according to claim 6, wherein the tyrosine kinase inhibitor is afatinib, canertinib, cetuximab, erlotinib, gefitinib, or lapatinib; or a pharmaceutically acceptable salt thereof, or a combination thereof.

8. The method according to claim 7, wherein the tyrosine kinase inhibitor is afatinib, or a pharmaceutically acceptable salt thereof.

9. The method according to claim 6, wherein the potassium channel is a $Ca^{2+}$-activated potassium channel.

10. The method according to claim 6 wherein said (R)—BPO-27 is administered as a racemic mixture with (S)—BPO-27.

* * * * *